(12) United States Patent
Lee

(10) Patent No.: US 9,517,240 B2
(45) Date of Patent: Dec. 13, 2016

(54) METHODS AND COMPOSITIONS FOR CANCER PREVENTION AND TREATMENT

(71) Applicant: THE REGENTS OF THE UNIVERSITY OF CALIFORNIA, Oakland, CA (US)

(72) Inventor: Eva Y. H. P. Lee, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/970,223

(22) Filed: Aug. 19, 2013

(65) Prior Publication Data

US 2013/0331365 A1 Dec. 12, 2013

Related U.S. Application Data

(63) Continuation-in-part of application No. 12/442,983, filed as application No. PCT/US2007/020753 on Sep. 26, 2007, now abandoned.

(60) Provisional application No. 60/847,173, filed on Sep. 26, 2006.

(51) Int. Cl.
| | | |
|---|---|---|
| A61K 31/56 | (2006.01) | |
| A61K 31/575 | (2006.01) | |
| A61K 31/567 | (2006.01) | |
| A61K 31/138 | (2006.01) | |
| A61K 31/565 | (2006.01) | |
| A61K 31/58 | (2006.01) | |
| A61K 31/566 | (2006.01) | |

(52) U.S. Cl.
CPC ........... *A61K 31/575* (2013.01); *A61K 31/138* (2013.01); *A61K 31/56* (2013.01); *A61K 31/565* (2013.01); *A61K 31/566* (2013.01); *A61K 31/567* (2013.01); *A61K 31/58* (2013.01)

(58) Field of Classification Search
None
See application file for complete search history.

(56) References Cited

U.S. PATENT DOCUMENTS

| | | | |
|---|---|---|---|
| 4,386,085 A | 5/1983 | Teutsch | |
| 4,519,946 A | 5/1985 | Teutsch | |
| 4,522,918 A | 6/1985 | Schlom | |
| 4,612,282 A | 9/1986 | Schlom | |
| 4,634,695 A | 1/1987 | Torelli | |
| 4,666,885 A | 5/1987 | Labrie | |
| 4,775,660 A | 10/1988 | Labrie | |
| 4,775,661 A | 10/1988 | Labrie | |
| 4,806,561 A | 2/1989 | Anderson | |
| 4,839,155 A | 6/1989 | McCague | |
| 4,978,657 A | 12/1990 | Teutsch | |
| 5,024,833 A | 6/1991 | Bianco | |
| 5,043,332 A | 8/1991 | Teutsch | |
| 5,089,488 A | 2/1992 | Ottow | |
| 5,224,886 A | 7/1993 | Cunningham | |
| 5,273,971 A | 12/1993 | Scholz | |
| 5,362,720 A | 11/1994 | Labrie | |
| 5,446,036 A | 8/1995 | Scholz | |
| 5,496,846 A | 3/1996 | Wilson | |
| 5,721,345 A | 2/1998 | Roberfroid | |
| 5,753,618 A | 5/1998 | Cavanak | |
| 5,759,766 A | 6/1998 | Nelson | |
| 5,766,571 A | 6/1998 | Ceriani | |
| 5,767,113 A | 6/1998 | Cohn | |
| 5,769,779 A | 6/1998 | Alderson | |
| 5,843,933 A | 12/1998 | Cleve | |
| 5,939,277 A | 8/1999 | Rakowicz-Szulczynska | |
| 5,962,444 A | 10/1999 | Cook | |
| 5,962,667 A | 10/1999 | Jain | |
| 5,981,201 A | 11/1999 | Avraham | |
| 6,015,805 A | 1/2000 | Cook | |
| 6,020,328 A | 2/2000 | Cook | |
| 6,066,616 A | 5/2000 | Cavanak | |
| 6,093,707 A | 7/2000 | Cook | |
| 6,096,301 A | 8/2000 | Bianco | |
| 6,096,718 A | 8/2000 | Weitzman | |
| 6,136,845 A | 10/2000 | Safe | |
| 6,150,421 A | 11/2000 | Gudas | |
| 6,179,766 B1 | 1/2001 | Dickerson | |
| 6,211,239 B1 | 4/2001 | Fontana | |
| 6,225,054 B1 | 5/2001 | Frudakis | |
| 6,262,042 B1 | 7/2001 | Cook | |
| 6,288,039 B1 | 9/2001 | Patierno | |
| 6,306,832 B1 | 10/2001 | Pietras | |
| 6,316,213 B1 | 11/2001 | O'Brien | |
| 6,342,483 B1 | 1/2002 | Holt | |
| 6,344,550 B1 | 2/2002 | Frudakis | |

(Continued)

OTHER PUBLICATIONS

Lu et al (Journal of Clinical Endocrinology & Metabolism 2006 vol. 91, No. 11: pp. 4514-4519).*
Poole et al (Science 2006, vol. 314, pp. 1467-1470).*
Lanari et al "Antiprogestins in breast cancer treatment: are we ready?" (Endocrine-Related Cancer 2012 vol. 19 pp. R35-R50).*
Holt et al in "Breast Cancer Genes: Therapeutic Strategies" (Annals New York Academy of Sciences: 1997: pp. 34-41).*
El Etreby et al in "Effect of antiprogestins and tamoxifen on growth inhibition of MCF-7 human breast cancer cells in nude mice" (Breast Cancer Research and Treatment: 1998: vol. 49, pp. 109-117.*
Dowsett et al (Breast Cancer Research and Treatment 2005 vol. 93: pp. S11-S18.*
Zheng et al., "BRCA1 mediates ligand-independent transcriptional repression of the estrogen receptor" 2001 Proc. Natl. Acad. Sci. 98:9587.
International Search Report and Written Opinion, mailed Mar. 25, 2008, for PCT/US2007/020753, 8 pages.

(Continued)

*Primary Examiner* — Catherine S Hibbert
(74) *Attorney, Agent, or Firm* — Casimir Jones, S.C.; Jason Bond

(57) ABSTRACT

The present invention provides methods of preventing or delaying the development of cancer (e.g., breast cancer) in BRCA1 mutation positive patients by beginning progesterone receptor antagonist treatment at an early age (e.g., by age 35, 30, or 25). In certain embodiment, such early treatment is long-term treatment, which may substitute or delay a preventative ovariectomy, single or double mastectomy (e.g., in patients wishing to delay or avoid a mastectomy, or patients that cannot afford a mastectomy).

13 Claims, 19 Drawing Sheets

(56) References Cited

U.S. PATENT DOCUMENTS

| | | |
|---|---|---|
| 6,358,682 B1 | 3/2002 | Jaffee |
| 6,368,796 B1 | 4/2002 | Avraham |
| 6,387,697 B1 | 5/2002 | Yuqiu |
| 6,399,328 B1 | 6/2002 | Vournakis |
| 6,410,507 B1 | 6/2002 | Reed |
| 6,423,496 B1 | 7/2002 | Frudakis |
| 6,429,186 B1 | 8/2002 | Fuh |
| 6,432,707 B1 | 8/2002 | Reed |
| 6,482,600 B1 | 11/2002 | Burmer |
| 6,489,101 B1 | 12/2002 | Dillon |
| 6,518,237 B1 | 2/2003 | Yuqiu |
| 6,528,054 B1 | 3/2003 | Jiang et al. |
| 6,562,380 B1 | 5/2003 | Kelly |
| 6,573,368 B2 | 6/2003 | Yuqiu |
| 6,579,973 B1 | 6/2003 | Yuqiu |
| 6,586,570 B1 | 7/2003 | Frudakis |
| 6,586,572 B2 | 7/2003 | Jiang et al. |
| 6,590,076 B1 | 7/2003 | Yuqiu |
| 6,602,907 B1 | 8/2003 | Miles |
| 6,620,801 B2 | 9/2003 | Cook |
| 6,638,727 B1 | 10/2003 | Hung |
| 6,638,975 B1 | 10/2003 | Miles |
| 6,656,480 B2 | 12/2003 | Retter |
| 6,680,197 B2 | 1/2004 | Jiang et al. |
| 6,690,976 B2 | 2/2004 | Fenn |
| 6,703,204 B1 | 3/2004 | Mutter |
| 6,703,426 B1 | 3/2004 | Miles |
| 6,713,503 B1 | 3/2004 | Miles |
| 6,756,477 B1 | 6/2004 | Jiang et al. |
| 6,768,925 B2 | 7/2004 | Fenn |
| 6,821,725 B1 | 11/2004 | Carrasco |
| 6,828,346 B2 | 12/2004 | Joshi-Hangal |
| 6,828,431 B1 | 12/2004 | Frudakis |
| 6,844,325 B2 | 1/2005 | Jiang et al. |
| 6,861,415 B2 | 3/2005 | Kim |
| 6,861,506 B1 | 3/2005 | Frudakis |
| 6,894,026 B1 | 5/2005 | Quay |
| 6,936,424 B1 | 8/2005 | Watkins |
| 6,958,361 B2 | 10/2005 | Houghton |
| 6,962,928 B2 | 11/2005 | Wallace |
| 6,969,518 B2 | 11/2005 | Houghton |
| 6,978,788 B2 | 12/2005 | Klimberg |
| 7,018,991 B2 | 3/2006 | Cook |
| 7,196,074 B2 | 3/2007 | Blye |
| 7,759,383 B2 | 7/2010 | Wang et al. |
| 2004/0048841 A1* | 3/2004 | Hoffmann et al. ........... 514/179 |
| 2007/0213306 A1 | 9/2007 | Hausknecht |

OTHER PUBLICATIONS

Blithe et al., "Development of the selective progesterone receptor modulator CDB-2914 for clinical indications," Steroids, 2003, 68:1013-1017.

Allan et al., 2006, "Molecular properties and preclinical pharmacology of JNJ-1250132, a steroidal progesterone receptor modulator that inhibits binding of the receptor to DNA in vitro," Steroids, 71:578-584.

An et al., 2006, "Steroid Receptor Coactivator-3 Is Required for Progesterone Receptor Trans-activation of Target Genes in Response to Gonadotropin-releasing Hormone Treatment of Pituitary Cells," J. Biol. Chem. 281:20817-24.

Bakker et al., "Comparison of the actions of the antiprogestin mifepristone (RU486), the progestin megestrol acetate, the LHRH analog buserelin, and ovariectomy in treatment of rat mammary tumors" 1987 Cancer Treat. Rep. 71:1021-1027.

Chabbert-Buffet et al., "Selective progesterone receptor modulators and progesterone antagonists: mechanisms of action and clinical applications" 2005 Hum. Repro. Update 11:293-307.

Clark et al., 2003, "Steroid receptors and proliferation in the human breast," Steroids 68:789-794.

Dowsett et al., "Biological characteristics of the pure antiestrogen fulvestrant: overcoming endocrine resistance" 2005 Breast Cancer Res. Treat. 93:11-18.

Etreby et al., "Effect of Antiprogestins and Tamoxifen on Growth Inhibition of MCF-7 Human Breast Cancer Cells in Nude Mice" 1998 Breast Cancer Res Treat vol. 49 No. 2 pp. 109-117.

Fan et al., 1999, "BRCA1 Inhibition of Estrogen Receptor Signaling in Transfected Cells," Science 284:1354-1356.

Fensome et al., "New progesterone receptor antagonists: 3,3-disubstituted-5-aryloxindoles" 2002 Bio. Med. Chem. Lett. 12:3487-90.

Fuhrmann et al., "Synthesis and biological activity of a novel, highly potent progesterone receptor antagonist" 2000 J. Med. Chem. 43:5010-5016.

Hedenfalk, "Gene-Expression Profiles in Hereditary Breast Cancer" 2001 New Eng. J. Med 344:539-548.

Henninghausen et al., "Information networks in the mammary gland" 2005 Nat. Rev. Mol. Cell.Biol. 6:715-25.

Jazaeri et al., "Gene expression profiles of BRCA1-linked, BRCA2-linked, and sporadic ovarian cancers" 2002 J. Nat. Cancer 25 Inst. 94:990-1000.

Jazaeri et al., "BRCA1-mediated repression of select X chromosome genes" 2004 J. Transl. Med. 2:32-39.

Jones et al., "Promotion of mammary cancer development by tamoxifen in a mouse model of Brca1-mutation-related breast cancer" 2005 Oncogene 24:3554-3562.

King et al., "Increased progesterone receptor expression in benign epithelium of BRCA1-related breast cancers" 2004 Cancer Res. 64:5051-5053.

Klijn et al., "Progesterone Antagonists and Progesterone Receptor Modulators in the Treatment of Breast Cancer" 2000 Steroids vol. 65 No. 2 pp. 825-830.

Kurata et al., "Endocrinological properties of two novel nonsteroidal progesterone receptor modulators, CP8816 and CP8863" 2005 J. Pharmacol. Exp. Ther. 313:916-20.

Labrie et al., "Em-652 (SCH57068), a third generation SERM acting as pure antiestrogen in the mammary gland and endometrium," 1999, J. Steroid. Biochem. Mol. Biol. 69:51-84.

Lakhani et al., "Multifactorial analysis of differences between sporadic breast cancers and cancers involving BRCA1 and BRCA2 mutations" 1998 J. Nat. Cancer Inst. 90:1138-1145.

Lange et al., "Phosphorylation of human progesterone receptors at serine-294 by mitogen-activated protein kinase signals their degradation by the 26S proteasome" 2000 Proc. Natl. Acad. Sci. 97:1032-1037.

Lee et al., "Postmenopausal hormone therapy and breast cancer risk: the Multiethnic Cohort" 2006 Int. J. Cancer 118:1285-91.

Li et al., "A contemporary understanding of progesterone receptor function" 2004 Mech. Ageing Dev. 125:669-678.

Li et al., "The SRC-3/AIB1 coactivator is degraded in a ubiquitin- and ATP-independent manner by the REGgamma proteasome" 2006 Cell 124:381-392.

Lin et al., "Somatic mutation of p53 leads to estrogen receptor alpha-positive and -negative mouse mammary tumors with high frequency of metastasis" 2004 Cancer Res. 64:3525-3532.

Ma et al., "The Breast Cancer Susceptibility Gene BRCA1 Regulates Progesterone Receptor Signaling in Mammary Epithelial Cells" 2006 Molecular Endocrinology vol. 20 No. 1 pp. 14-34.

Mallepell et al., "Paracrine signaling through the epithelial estrogen receptor alpha is required for proliferation and morphogenesis in the mammary gland" 2006 Proc. Natl. Acad. Sci. 103:2196-2201.

Michna et al., "The antitumor mechanism of progesterone antagonists is a receptor mediated antiproliferative effect by induction of terminal cell death" 1989 J. Steroid Biochem. 34:447-453.

Miki et al., "A strong candidate for the breast and ovarian cancer susceptibility gene BRCA1" 1994 Science 266:66-71.

Beral et al., "Breast cancer and hormone-replacement therapy in the Million Women Study" 2003 Lancet 362:419-427.

Mulac-Jericevic et al., "Defective mammary gland morphogenesis in mice lacking the progesterone receptor B isoform" 2003 Proc. Natl. Acad. Sci. 100:9744-9749.

Osborne et al., "Role of the estrogen receptor coactivator AIB1 (SRC-3) and HER-2/neu in tamoxifen resistance in breast cancer" 2003 J. Nat. Cancer Inst. 95:353-361.

Xu et al., "Progesterone receptor modulator CDB-2914 down-regulates vascular endothelial growth factor, adrenomedullin and their

(56) References Cited

OTHER PUBLICATIONS receptors and modulates progesterone receptor content in cultured human uterine leiomyoma cells," 2006, Hum. Repro. 21:2408-16.

Xu et al., "Progesterone Receptor Modulator CDB-2914 Down-Regulates Proliferative Cell Nuclear Antigen and Bcl-2 Protein Expression and Up-Regulates Caspase-3 and Poly (Adenosine 5'-Diphosphate-ribose) Polymerase Expression in Cultured Human Uterine Leiomyoma Cells," 2005, J. Clin. Endo. & Metab. 90:953-961.

Rao and Miller, "Hormonal therapy in epithelial ovarian cancer" 2006 Exp. Rev. Anticancer Ther. 6:43-7.

Rao et al., "A practical large-scale synthesis of 17alpha-acetoxy-11beta-(4-N, N-dimethylaminophenyl)-19-norpregna-4,9-diene-3,20-dione (CDB-2914)" 2000 Steroids 65:395-400.

Razandi et al., "BRCA1 inhibits membrane estrogen and growth factor receptor signaling to cell proliferation in breast cancer" 2004 Mol. Cell. Biol. 24:5900-13.

Robertson et al., "Onapristone, a Progesterone Receptor Antagonist, as First-line Therapy in Primary Breast Cancer," 1999, Eur. J. Cancer 35:214-218.

Rosenberg et al., "Is ICI 182,780 an antiprogestin in addition to being an antiestrogen?" 2000, Breast Cancer Res 60:1-8.

Rossouw et al., "Risks and benefits of estrogen plus progestin in healthy postmenopausal women: principal results From the Women's Health Initiative randomized controlled trial" 2002, JAMA 288:321-333.

Schneider et al., "Tumor-inhibiting potential of ZK 112.993, a new progesterone antagonist, in hormone-sensitive, experimental rodent and human mammary tumors" 1990 Anticancer Res. 10:683-687.

Schneider et al., "Antitumor activity and mechanism of action of different antiprogestins in experimental breast cancer models" 1990 J. Steroid Biochem. Mol. Biol. 37:783-787.

Shyamala et al., "Transgenic mice carrying an imbalance in the native ratio of A to B forms of progesterone receptor exhibit developmental abnormalities in mammary glands" 1998 Proc. Natl. Acad. Sci. 95:696-701.

Tabata et al., "CP8668, a novel orally active nonsteroidal progesterone receptor modulator with tetrahydrobenzindolone skeleton" 2003 Eur. J. Pharmacol. 461:73-8.

Terefenko et al., "SAR studies of 6-aryl-1,3-dihydrobenzimidazol-2-ones as progesterone receptor antagonists" 2005 Bio. Med. Chem. Lett. 15:3600-3603.

Thompson et al., "Decreased expression of BRCA1 accelerates growth and is often present during sporadic breast cancer progression" 1995 Nat. Genet. 9:444-450.

Ting et al., "The DNA double-strand break response pathway: becoming more BRCAish than ever" 2004 DNA Repair 3:935-944.

Turner et al., "Hallmarks of 'BRCAness' in sporadic cancers" 2004 Nat. Rev. Cancer 4:814-819.

Van Den Berg et al., "The relationship between affinity of progestins and antiprogestins for the progesterone receptor in breast cancer cells (ZR-PR-LT) and ability to down-regulate the receptor: evidence for heterospecific receptor modulation via the glucocorticoid receptor" 1993 Eur. J. Cancer 29A:1771-75.

Xu et al., "Conditional mutation of Brca1 in mammary epithelial cells results in blunted ductal morphogenesis and tumour formation" 1999 Nat. Genet. 22:37-43.

* cited by examiner

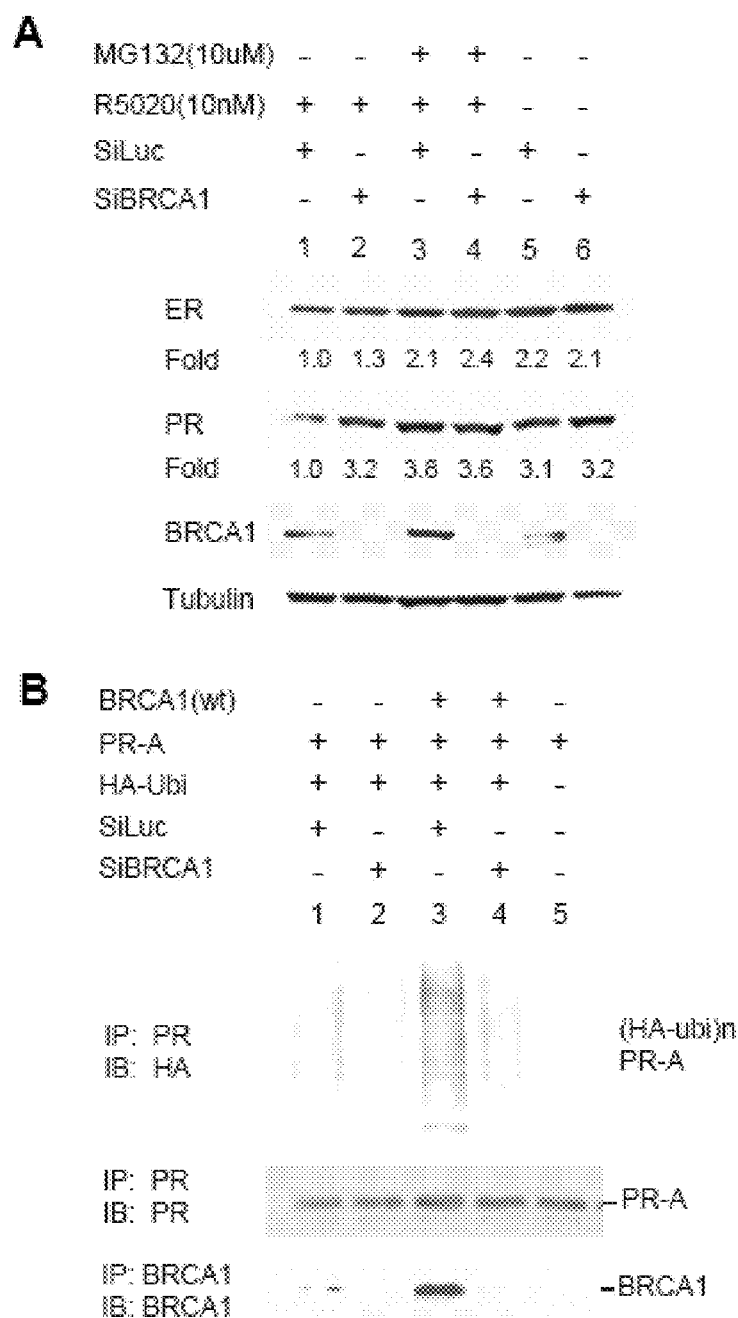

```
                          SEQUENCE LISTING

<160> NUMBER OF SEQ ID NOS: 12

<210> SEQ ID NO 1
<211> LENGTH: 21
<212> TYPE: DNA
<213> ORGANISM: Artificial sequence
<220> FEATURE:
<223> OTHER INFORMATION: DNA PRIMER

<400> SEQUENCE: 1
ctggggtgga ggtcgtacaa g                                              21

<210> SEQ ID NO 2
<211> LENGTH: 22
<212> TYPE: DNA
<213> ORGANISM: Artificial sequence
<220> FEATURE:
<223> OTHER INFORMATION: DNA PRIMER

<400> SEQUENCE: 2
accaattgcc ttgatcaatt cg                                             22

<210> SEQ ID NO 3
<211> LENGTH: 24
<212> TYPE: DNA
<213> ORGANISM: Artificial sequence
<220> FEATURE:
<223> OTHER INFORMATION: DNA PRIMER

<400> SEQUENCE: 3
tcgtctgtag tctcgcctat accg                                           24

<210> SEQ ID NO 4
<211> LENGTH: 21
<212> TYPE: DNA
<213> ORGANISM: Artificial sequence
<220> FEATURE:
<223> OTHER INFORMATION: DNA PRIMER

<400> SEQUENCE: 4
cggagggagt caacaacgag t                                              21

<210> SEQ ID NO 5
<211> LENGTH: 21
<212> TYPE: DNA
<213> ORGANISM: Artificial sequence
<220> FEATURE:
<223> OTHER INFORMATION: DNA PRIMER

<400> SEQUENCE: 5
cattgacctt cactacatgg t                                              21

<210> SEQ ID NO 6
<211> LENGTH: 20
<212> TYPE: DNA
<213> ORGANISM: Artificial sequence
<220> FEATURE:
<223> OTHER INFORMATION: DNA PRIMER

<400> SEQUENCE: 6
```
acccttcaag tgagccccag                                              20

<210> SEQ ID NO 7
<211> LENGTH: 24
<212> TYPE: DNA
<213> ORGANISM: Artificial sequence
<220> FEATURE:
<223> OTHER INFORMATION: DNA PRIMER

<400> SEQUENCE: 7
accgtttgac accaccaaca acag                                         24

<210> SEQ ID NO 8
<211> LENGTH: 24
<212> TYPE: DNA
<213> ORGANISM: Artificial sequence
<220> FEATURE:
<223> OTHER INFORMATION: DNA PRIMER

<400> SEQUENCE: 8
tgggtccttc gctggattag gttt                                         24

<210> SEQ ID NO 9
<211> LENGTH: 20
<212> TYPE: DNA
<213> ORGANISM: Artificial sequence
<220> FEATURE:
<223> OTHER INFORMATION: DNA PRIMER

<400> SEQUENCE: 9
ggtggaggtc gtacaagcat                                              20

<210> SEQ ID NO 10
<211> LENGTH: 20
<212> TYPE: DNA
<213> ORGANISM: Artificial sequence
<220> FEATURE:
<223> OTHER INFORMATION: DNA PRIMER

<400> SEQUENCE: 10
ggatttgcca catggtaagg                                              20

<210> SEQ ID NO 11
<211> LENGTH: 20
<212> TYPE: DNA
<213> ORGANISM: Artificial sequence
<220> FEATURE:
<223> OTHER INFORMATION: DNA PRIMER

<400> SEQUENCE: 11
cggagaagga cagcagactc                                              20

<210> SEQ ID NO 12
<211> LENGTH: 20
<212> TYPE: DNA
<213> ORGANISM: Artificial sequence
<220> FEATURE:
<223> OTHER INFORMATION: DNA PRIMER

<400> SEQUENCE: 12
cccaaagaga caccaggaag                                              20

METHODS AND COMPOSITIONS FOR CANCER PREVENTION AND TREATMENT

This application is a Continuation-in-part of U.S. application Ser. No. 12/442,983 Mar. 4, 2010, which is a §371 National Entry of International Patent Application PCT/US2007/020753, filed Sep. 26, 2007, which claims priority to U.S. Provisional Application 60/847,173, filed on Sep. 26, 2006, each of which are herein incorporated by reference in their entireties.

This application was made with government support under grant number CA049649 awarded by National Institutes of Health and grant number DAMD17-02-1-0694 awarded by the Department of Defense. The government has certain rights to this invention.

FIELD OF THE INVENTION

The present invention provides methods of preventing or delaying the development of cancer (e.g., breast cancer) in BRCA1 mutation positive patients by beginning progesterone receptor antagonist treatment at an early age (e.g., by age 35, 30, or 25). In certain embodiment, such early treatment is long-term treatment, which may substitute or delay a preventative single or double mastectomy (e.g., in patients wishing to delay or avoid a mastectomy, or patients that cannot afford a mastectomy).

BACKGROUND OF THE INVENTION

Breast cancer incidence in women has increased from one in 20 in 1960 to one in seven today. Every two minutes a woman in the United States is diagnosed with breast cancer. In 2005, it was estimated that about 212,000 new cases of invasive breast cancer would be diagnosed, along with 58,000 new cases of non-invasive breast cancer, and 40,000 women were expected to die from this disease. The exact cause of breast cancer is not known, however changes in certain genes make women more susceptible to breast cancer.

Individuals with mutations in the breast cancer gene 1 (BRCA1) and gene 2 (BRCA2), for example, are predisposed to breast and ovarian cancers and run a high risk of having the disease. BRCA1 participates in several cellular processes, but its function in suppressing carcinogenesis of ovarian hormone-sensitive tissues remains unclear. Historically, estrogen and the estrogen receptor and their function in breast cancer have attracted considerable attention. However, the underlying mechanisms of cancer are not fully understood.

The current therapies for breast cancer include chemotherapy, radiation therapy, surgery to remove a woman's ovaries to decrease production of the hormones estrogen and progesterone, surgery to remove the tumors, and combinations thereof. What is needed are novel ways of studying, understanding, treating, and above all, preventing breast and other cancers.

SUMMARY OF THE INVENTION

The present invention provides methods of preventing or delaying the development of cancer (e.g., breast cancer) in BRCA1 mutation positive patients by beginning progesterone receptor antagonist treatment at an early age (e.g., by age 35, 30, or 25). In certain embodiment, such early treatment is long-term treatment, which may substitute or delay a preventative single or double mastectomy (e.g., in patients wishing to delay or avoid a mastectomy, or patients that cannot afford a mastectomy).

Mutations in BRCA1 are associated with an increase in breast and ovarian cancer risks (Miki et al., 1994, Science 266:66). Reduced BRCA1 expression due to promoter methylation is also found in sporadic breast and ovarian cancers (Thompson et al., 1995, Nat. Genet. 9:444). BRCA1 maintains genome stability by participating in DNA damage repair, cell cycle checkpoint control and transcriptional regulation (Ting et al., 2004, DNA Repair 3:935; Turner et al., 2004, Nat. Rev. Cancer 4:814). The specific suppression of breast and ovarian carcinogenesis by the pleiotropic BRCA1 tumor suppressor may be due to its regulatory roles over estrogen receptor α (ERα) and the progesterone receptor (PR) (Fan et al., 1999, Science 284:1354; Zheng et al., 2001, Proc. Natl. Acad. Sci. 98:9587; Razandi et al., 2004, Mol. Cell. Biol. 24:5900; Ma et al., 2006, Mol. Endocrinol. 20:14).

ERα and PR play important roles in breast development (Henninghausen et al., 2005, Nat. Rev. Mol. Cell. Biol. 6:715; Li et al., 2004, Mech. Ageing Dev. 125:669). In ERα knockout mice, ductal elongation and pregnancy-induced proliferation of mammary gland are severely affected (Mallepell et al., 2006, Proc. Natl. Acad. Sci. 103:2196). In mice lacking PR-B, the long form of PR, ductal elongation is normal but pregnancy-induced ductal branching, and alveolar proliferation and differentiation are defective (Mulac-Jericevic et al., 2003, Proc. Natl. Acad. Sci. 100:9744). BRCA1 modulates the activities of these nuclear hormone receptors through three distinct mechanisms: ligand-dependent, and -independent transcription activities of ERα and PR, as well as non-genomic function of ERα (Fan et al., 1999, Science 284:1354; Zheng et al., 2001, Proc. Natl. Acad. Sci. 98:9587; Razandi et al., 2004, Mol. Cell. Biol. 24:5900; Ma et al., 2006, Mol. Endocrinol. 20:14). The contribution of ER and PR in BRCA1-mediated carcinogenesis remains unclear, however.

Progesterone and estrogen hormone replacement therapy in postmenopausal women is associated with higher proliferation index and significantly greater breast cancer risk (Million Women Study, 2003, Lancet 362:419; Rossouw et al., 2002, JAMA 288:321; Lee et al., 2006, Int. J. Cancer 118:1285). The two PR isoforms, PR-A and PR-B are generated through alternative promoter usage of a single gene (Li et al., 2004, Mech. Ageing Dev. 125:669). Introduction of extra PR-A transgene, the short form of PR in mice, leads to abnormal mammary development and ductal hyperplasia (Shyamala et al., 1998, Proc. Natl. Acad. Sci. 95:696). Immunostaining shows increased PR expression in normal mammary epithelial cells (MECs) of breast cancer patients carrying a germ line mutation of BRCA1 (King et al., 2004, Cancer Res. 64:5051). Normally, PR stability is regulated by proteosome; a progesterone receptor becomes polyubiquinated upon exposure to a ligand and is subsequently targeted for degradation by proteosome (Lange et al., 2000, Proc. Natl. Acad. Sci. 97:1032).

The present invention demonstrates that progesterone receptor stability is related to breast cancer, and preventing and/or treating progesterone related breast cancer with anti-progesterones provides a molecular framework for the study and prevention of cancer in BRCA1 carriers by using anti-progesterones as a chemopreventive strategy for PR related cancers. Anti-progesterones, such as pure progesterone receptor antagonists (PAs, typically associated with compounds that exhibit no agonistic effect on PR) or selective progesterone receptor modulators (SPRMs, typically associated with compounds that exhibit both antagonistic and agonist effects of PR) (hereinafter, PA and SPRM compounds will be referred to under the general acronym of "SPRM") are those compounds, drugs, or agents that modulate the activity of the progesterone receptor (Chabbert-buffet et al., 2005, Hum. Repro. Update 11:293-307, incorporated herein in its entirety). Although the SPRMs have no immediate structural relationship with progesterone, they are stereochemically similar to this hormone and interact with its receptors. The study of BRCA1 mutations in vitro and in an in vivo mouse model described herein demonstrates the efficacy of using SPRMs to modulate tumorigenesis.

Using mice models, it is shown that BRCA1/p53 defective mammary glands of nulliparous mice accumulate lateral branches and undergo extensive alveologenesis, a phenotype only seen during pregnancy in normal mice. The majority of BRCA1 mediated tumors in humans harbor p53 mutations as well (Ting et al., 2004, DNA Repair 3:935; Turner et al., 2004, Nat. Rev. Cancer 4:814). Progesterone receptors, but not estrogen receptors, are over-expressed in MECs of conditional BRCA1/p53, but not p53 knockout mice; therefore, progesterone is a potent mitogen for BRCA1/p53 defective MECs specifically. Ligand-induced polyubiquitination and proteosome-mediated degradation of PRs are aberrant in breast epithelial cells with BRCA1 knockdown, leading to stabilization and accumulation of PR. Treatment with the SPRM mifepristone prevents tumorigenesis in mice carrying mutated BRCA1/p53 alleles, thereby showing a critical role of PR in BRCA1 mediated tumorigenesis. A tissue-specific function of BRCA1 is consistent with increased breast cancer risk observed in menopausal progesterone-estrogen therapy.

The present invention is not limited to a particular mechanism. Indeed, an understanding of the mechanism is not necessary to practice the present invention. Nonetheless, it is contemplated that selective progesterone receptor modulators reduce breast cancer risk, especially in BRCA1 carriers. Hormone receptors have also been associated with ovarian cancers (Rao and Miller, 2006, Exp. Rev. Anticaner Ther. 6:43-7). As such, treatment and prevention of cancers using SPRMs is not limited to breast cancers. Indeed, the treatment and prevention is contemplated to be effective for ovarian cancers and other cancers that demonstrate high risk because of the predisposition of the patient to have a dysfunctional BRCA1 and/or p53 gene. It is contemplated that BRCA2 related cancers could also benefit from the administration of SPRMs, as most BRCA2 related tumors are positive for both estrogen and progesterone receptors (Hedenfalk, 2001, New Eng. J. Med 344:539). Prevention of cancer relapse using SPRMs is also contemplated by application of the methods and compositions of the present invention. For example, it is contemplated that once a cancer has been eradicated, compositions and methods of the present invention are employed to prevent or diminish the possibility of cancer recurrence.

There are several subclasses of tumors that are BRCA1-like and BRCA-2 like. These tumors are similar to hereditary BRCA tumorigenesis, but instead of being germline in origin they are instead sporadic tumors, in that they are not hereditary. It has been suggested that these sporadic tumor subclasses utilize the same or similar cellular molecular pathways as the BRCA genes, and these tumors have been found to cause both breast and ovarian cancers (Jazaeri et al., 2004, J. Transl. Med. 2:32; Jazaeri et al., 2002, J. Nat. Cancer Inst. 94:990; Hedenfalk et al., 2001, N. Engl. J. Med. 344:539; Lakhani et al., 1998, J. Nat. Cancer Inst. 90:1138).

It is contemplated that these types of BRCA-like breast and ovarian cancers are also treatable by the methods of the present invention.

Treatments of the present invention need not target PR directly. Indirect methods that alter PR activity or signaling are also contemplated for use in the compositions and methods of the present invention. For example, the steroid receptor co-activator protein 3 (SRC3, also known as AIB1) is an estrogen receptor co-activator that is frequently over-expressed in breast cancer and can reduce the antagonistic activity of tamoxifen thereby decreasing the drugs efficacy in treating cancer (Osborne et al., 2003, J. Nat. Cancer Inst. 95:353; Li et al., 2006, Cell 124:381). SRC3 is over-expressed in breast cancer cells compared with normal duct epithelial cells and is amplified in breast tumors. SRC3 is also thought to be a PR co-activator (An et al., 2006, J. Biol. Chem. [E-pub ahead of time, May 24]), and therefore plays a role in PR related cancers. It is contemplated that targeting SRC3 causes a decrease in PR activity, thereby providing a useful treatment of PR related cancers either alone, or in combination with established cancer therapies.

Methods of treatment and/or prevention of progesterone receptor related cancers with SPRMs herein described are used alone or in conjunction with established cancer and therapy regimens. Other drugs, compounds, treatment and therapy regimens for combating breast and/or ovarian cancer include, but are not limited to, those methods and compositions encompassed in U.S. Pat. Nos. 7,018,991, 6,861,415, 6,620,801, 6,150,421, 6,262,042, 6,093,707, 6,020,328, 6,015,805, 6,962,928, 6,562,380, 4,839,155, 6,690,976, 6,768,925, 5,769,779, 6,179,766, 5,362,720, 5,024,833, 6,638,727, 6,096,301, 4,806,561, 6,978,788, 6,288,039, 4,775,660, 4,666,885, 6,894,026, 6,211,239, 5,721,345, 5,496,846, 4,775,661, 6,936,424, 6,861,506, 6,844,325, 6,821,725, 6,713,503, 6,703,426, 6,656,480, 6,638,975, 6,602,907, 6,590,076, 6,586,570, 6,579,973, 6,573,368, 6,518,237, 6,423,496, 6,399,328, 6,387,697, 6,344,550, 6,225,054, 6,136,845, 6,066,616, 5,962,667, 5,939,277, 5,766,571, 5,759,766, 5,753,618, 6,969,518, 6,958,361, 6,828,346, 6,828,431, 6,756,477, 6,703,204, 6,680,197, 6,586,572, 6,528,054, 6,489,101, 6,482,600, 6,432,707, 6,429,186, 6,410,507, 6,368,796, 6,358,682, 6,342,483, 6,316,213, 6,306,832, 6,096,718, 5,962,444, 5,843,933, 5,767,113, 5,446,036, 5,273,971, 5,224,886, 5,089,488, 5,981,201, 5,043,332, 4,978,657, 4,634,695, 4,612,282, 4,522,918, 4,519,946, 4,386,085, and found in references Robertson et al., 1999, Eur. J. Cancer 35:214; Allan et al., 2006, Steroids April 3 [Epub ahead of print]; Michna et al., 1989, J. Steroid Biochem. 34:447; Fuhrmann et al., 2000, J. Med. Chem. 43:5010; Rosenberg et al., 2000, Breast Cancer Res 60:1; van den Berg et al., 1993, Eur. J. Cancer 29A: 1771; Schneider et al., 1990, J. Steroid Biochem. Mol. Biol. 37:783; Schneider et al., 1990, Anticancer Res. 10:683; El Etreby et al., 1998, Breast Cancer Res. Treat. 49:109; Klijn et al., 2000, Steroids 65:825; Bakker et al., 1987, Cancer Treat. Rep. 71:1021, all patents and references are incorporated herein in their entireties.

In one embodiment, the present invention is a method for preventing progesterone receptor related cancers comprising providing a subject with a hereditary cancer gene mutation that is progesterone receptor related, providing an antagonist of the progesterone receptor, and treating said subject with said antagonist thereby preventing said progesterone receptor related cancer. In some embodiments, the cancer gene is breast cancer gene 1. In some embodiments, the antagonist of the progesterone receptor is a selective progesterone receptor modulator, and is preferably mifepristone. In some embodiments, the subject is further treated with an additional chemopreventive agent, wherein that chemopreventive agent is preferably an anti-estrogen and/or an aromatase inhibitor. In a preferred embodiment, the anti-estrogen is tamoxifen. In a preferred embodiment, the anti-estrogen is fulvestrant.

In one embodiment, the present invention is a method of treating a progesterone receptor related cancer comprising providing a subject diagnosed with a progesterone receptor related cancer, providing an antagonist of the progesterone receptor, and administering said progesterone receptor antagonist to said subject to treat said progesterone receptor related cancer. In some embodiments, the progesterone receptor related cancer is a hereditary cancer, while in other embodiments the progesterone receptor related cancer is a sporadic cancer. In some embodiments, the hereditary cancer is caused by a BRCA gene mutation. In some embodiments, the antagonist of the progesterone receptor is a selective progesterone receptor modulator, and is preferably mifepristone. In some embodiments, the treating of the progesterone related cancer further comprises an administration of an additional anticancer agent.

In some embodiments, the present invention provides method for preventing progesterone receptor related cancers comprising: a) providing a subject with a breast cancer gene 1 (BRCA1) mutation that is progesterone receptor related, wherein the subject is less than 35 years old (e.g., less than 35 . . . 31 . . . 27 . . . 25 . . . 18; or 21-28 years old) and, optionally, does not have detectable progesterone receptor related cancer; b) providing a progesterone receptor antagonist, and c) treating the subject with the progesterone receptor antagonist thereby preventing, or delaying the onset of, the progesterone receptor related cancer.

In certain embodiments, the subject has been diagnosed as possessing the BRCA1 mutation (e.g., a doctor or other health care provided has analyzed the subject's DNA and determined that it possesses at least one cancer related mutation in the BRCA1 gene). In other embodiments, the subject has been diagnosed as likely to have the BRCA1 mutation based on family history (e.g., mother, grandmother, aunt, and or/sister have BRCA1 mutation caused breast cancer). In particular embodiments, the subject is less than 30 years old and does not have detectable progesterone receptor related cancer. In further embodiments, the subject is less than 25 years old and does not have detectable progesterone receptor related cancer.

In particular embodiments, the antagonist of the progesterone receptor is a selective progesterone receptor modulator. In certain embodiments, the selective progesterone receptor modulator comprises mifepristone. In additional embodiments, the selective progesterone receptor modulator comprises 17α-acetoxy-11β-(4-N,N-dimethylaminophenyl)-19-norpregna-4,9-diene-3,20-dione (CDB-2914).

In some embodiments, the methods further comprise treating the subject with an additional chemopreventive agent. In additional embodiments, the chemopreventive agent is an anti-estrogen. In other embodiments, the chemopreventive agent is an aromatase inhibitor. In particular embodiments, the anti-estrogen is tamoxifen or fulvestrant.

In particular embodiments, the treating comprises administering 1-75 mg per day of the progesterone receptor antagonist daily for at least 2 months (e.g., 2 months . . . 6 months . . . 9 months . . . 1 year . . . 1.8 years . . . 2.7 years . . . 4.0 years . . . or at least 5 years). In some embodiments, the treating comprises administering 1-75 mg per day of the progesterone receptor antagonist daily for at least 5 years. In particular embodiments, the progesterone receptor antagonist comprises ZK137316 and/or ZK230211.

In additional embodiments, the progesterone receptor antagonist comprises J1042 or Onapristone. In certain embodiments, the progesterone receptor antagonist comprises Asoprisnil (J-867). In further embodiments, the progesterone receptor antagonist comprises Org 31710 and/or Org 33628. In some embodiments, the progesterone receptor antagonist comprises CBD-4124.

DEFINITIONS

Figure 1:
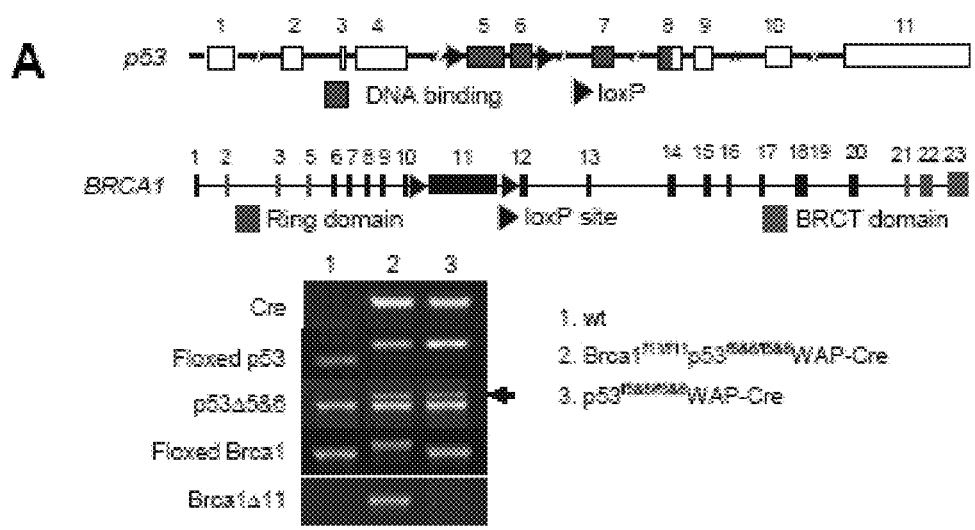
FIGS. 1A-1D show that mutation in BRCA1/p53 leads to increased mammary ductal branching and alveologenesis; (A) Schematic representation of floxed BRCA1 and p53 alleles, and PCR based analyses showing deletion of these alleles in the mammary gland of mice of all genotypes. Ring and BRCT domains of BRCA1 and DNA binding domain of p53 are shown. (B) Whole mounts of mammary glands from wild-type (a,b), $p53^{\Delta 5 \& 6}$ (c,d), and $BRCA1^{\Delta 11/}p53\Delta^{5\&6}$ (e,f) mice were compared at 2.5 months of age; the number of branching points of the mammary gland were determined. The data represents average of branch points in five randomly selected areas±SD. (*$P \leq 0.05$). (C) Alveolar development in 4 months old $p53^{\Delta 5 \& 6}$ (a) and $BRCA1^{\Delta 11/}p53^{\Delta 5 \& 6}$ (b) mice. (D) Proliferation of mammary epithelial cells at different estrous phases. Mice at the proestrous or estrous phase were injected intraperitoneally with 50 μg/per gram body weight of 5-bromo-2-deoxyuridine (BrdU). Mammary glands were fixed 2 hr post BrdU injection. Proliferating cells were identified by immunostaining with anti-BrdU antibody. The histogram shows the average number of BrdU labeled cells per duct. At least 15 mammary ducts/animal were evaluated (a minimum of three mice per genotype).
Figure 1:
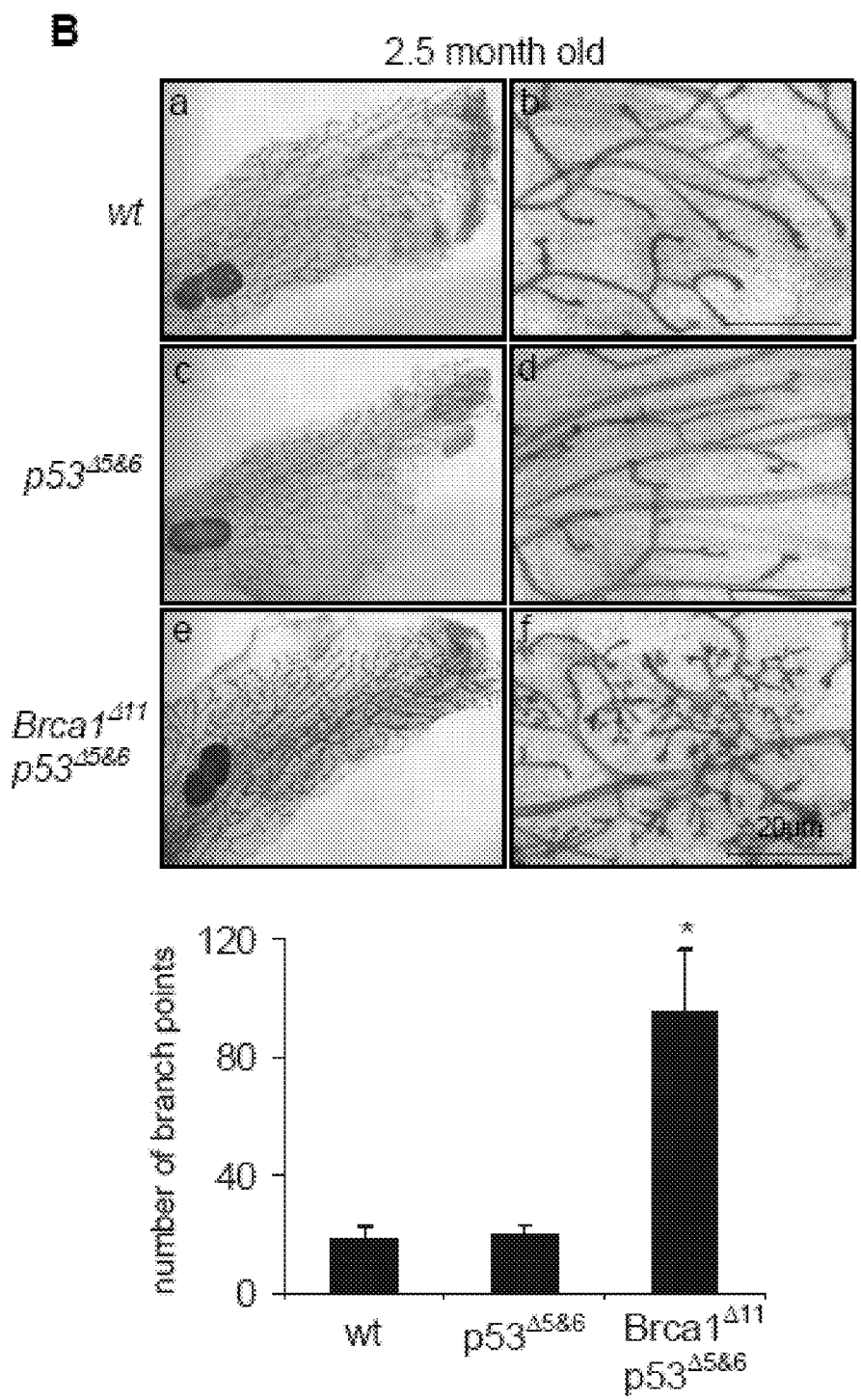
Figure 1:
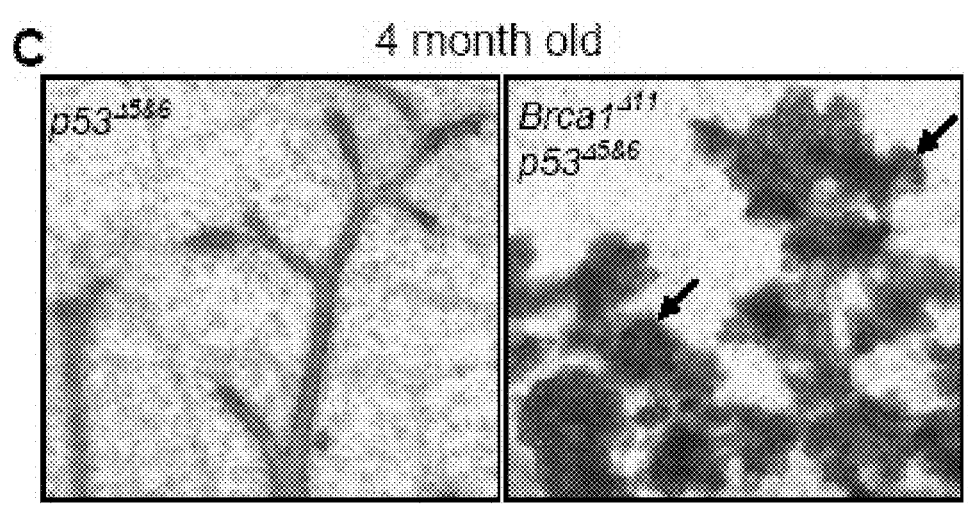
Figure 1:
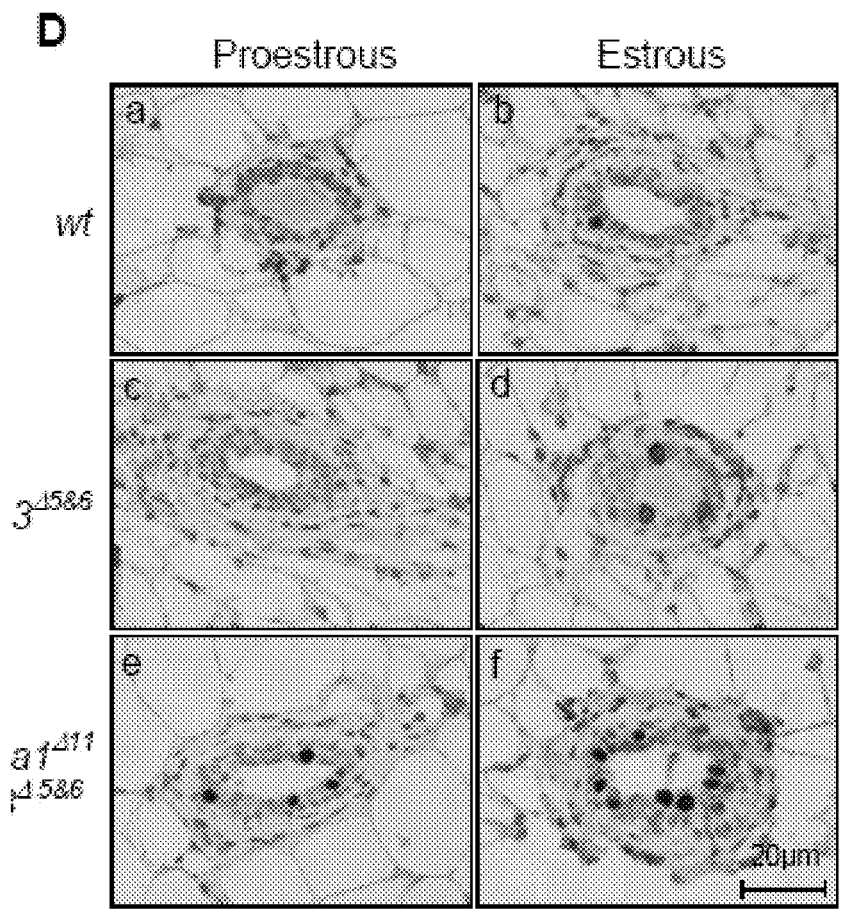
Figure 1:
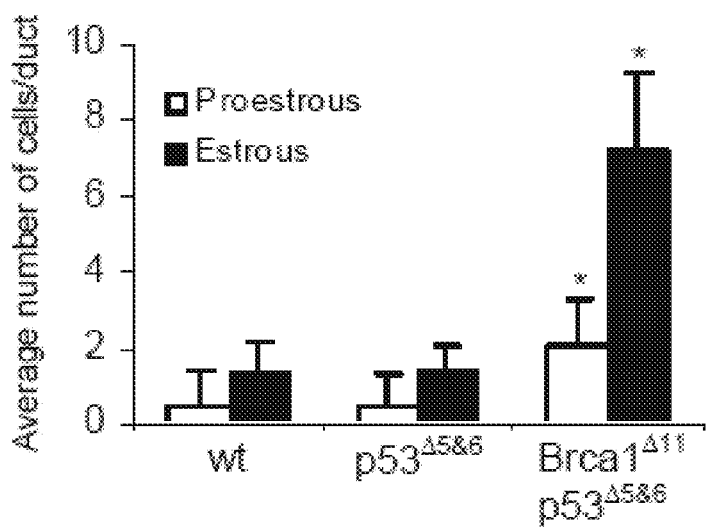

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include tissues and blood products, such as plasma, serum and the like. Such examples are not however to be construed as limiting the sample types applicable to the present invention.

As used herein, the term "peptide" refers to a compound comprising from two or more amino acid residues wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g. solid phase synthesis) or molecular biology techniques (see Sambrook, J. et al., Molecular Cloning: A Laboratory Manual, Cold Spring Harbor Press, Cold Spring Harbor, N.Y. (1989)).

As used herein, the term "peptidomimetic" refers to molecules which are not polypeptides, but which mimic aspects of their structures. For example, polysaccharides can be prepared that have the same functional groups as peptides. A peptidomimetic comprises at least two components, the binding moiety or moieties, and the backbone or supporting structure.

As used herein, the term "antibody" encompasses both monoclonal and polyclonal full-length antibodies and functional fragments thereof (e.g. maintenance of binding to target molecule). Antibodies can include those that are chimeric, humanized, primatized, veneered or single chain antibodies.

As used herein, the terms "RNA interference" and "RNAi" refer to a process whereby double stranded RNA inhibits gene expression in a sequence dependent manner. Small interfering RNA (siRNA) are small fragments (e.g., about 18-30 nucleotides in length) of sequence specific double stranded RNA whereby introduction of a sequence specific siRNA (e.g., substantially homologous or substantially complementary to the target RNA) into a subject results in post-transcriptional inhibition (e.g., mRNA is not translated into a protein product) of target mRNA, thereby regulating target gene expression. SiRNAs may also contain additional sequences, for example, linking sequences or loops, as well as stem and other folding structures. The gene to be silenced may be endogenous or exogenous to the organism. The expression of the gene is either completely or partially inhibited. For example, in the present invention RNA interference occurs when BRCA1 specific siRNA (siBRCA1) is utilized to inhibit expression of the BRCA1 gene.

As used herein, the term "effective amount" of a therapeutic compound (e.g. agent, compound, or drug) is an amount sufficient to achieve a desired therapeutic and/or prophylactic effect, such as to prevent or inhibit cancer tumor growth.

As used herein, the terms "agent", "compound" or "drug" are used to denote a compound or mixture of chemical compounds, a biological macromolecule such as an antibody, a nucleic acid, or an extract made from biological materials such as bacteria, plants, fungi, or animal (particularly mammalian) cells or tissues that are suspected of having therapeutic properties. The compound, agent or drug may be purified, substantially purified or partially purified.

As used herein, the term "fragment" when in reference to a protein (e.g. "a fragment of a given protein") refers to portions of that protein. The fragments may range in size from two amino acid residues to the entire amino acid sequence minus one amino acid. In one embodiment, the present invention contemplates "functional fragments" of a protein. Such fragments are "functional" if they can bind with their intended target protein (e.g. the functional fragment may lack the activity of the full length protein, but binding between the functional fragment and the target protein is maintained).

As used herein, the term "antagonist" refers to molecules or compounds (either native or synthetic) that inhibit the action of a compound (e.g., receptor channel, ligand, etc.). Antagonists may or may not be homologous to these compounds in respect to conformation, charge or other characteristics. Thus, antagonists may be recognized by the same or different receptors that are recognized by an agonist. Antagonists may have allosteric effects that prevent the action of an agonist. Or, antagonists may prevent the function of the agonist.

As used herein, the term "therapeutically effective amount" refers to that amount of the therapeutic agent sufficient to result in amelioration of one or more symptoms of a disorder, or prevent advancement of a disorder, or cause regression of the disorder, or prevent the disorder from occurring. For example, with respect to the treatment of cancer, a therapeutically effective amount preferably refers to the amount of a therapeutic agent that prevents tumors from occurring, decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

As used herein, the term "subject" refers to any biological entity that can be used for experimental work. For example, a "subject" can be a mammal such as a mouse, rat, pig, dog, and non-human primate. Preferably the subject is a human.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors, for example a mutation in BRCA1 or BRCA2 genes. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer, such as carriers of BRCA mutations, or a family history of cancer. Risk factors include, but are not limited to, gender, age, genetic predisposition, environmental exposure, prior incidents of cancer, preexisting noncancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the terms "anticancer agent" and "anticancer drug" refer to any therapeutic agents (e.g., chemotherapeutic compounds and/or molecular therapeutic compounds), radiation therapies, or surgical interventions, used in the treatment of hyperproliferative diseases such as cancer (e.g., in mammals).

As used herein, the term "hyperproliferative disease" refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

As used herein, the terms "prevent," "preventing," and "prevention" refer to stopping a hyperproliferative disease from starting or decreases the occurrence of pathological cells (e.g., hyperproliferative or neoplastic cells) and/or tumorigenesis in an animal. The prevention may be complete, e.g., the total absence of pathological cells and/or tumorigenesis in a subject. The prevention may also be partial, such that the occurrence of pathological cells and/or tumorigenesis in a subject is less than that which would have occurred without the present invention.

As used herein "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening, using the screening methods of the present invention. A known therapeutic compound refers to a therapeutic compound that has been shown (e.g., through animal trial or prior experience with administration to humans) to be effective in such treatment or prevention.

As used herein, the term "chemotherapeutic agent" refers to any compound, drug, or agent used to treat various forms of cancer. Chemotherapeutic agents have the ability to inhibit cancer cell growth and/or kill cancer cells. Chemotherapeutic agents to be used in conjunction with the compounds of the present invention, include but are not limited to, additional oncolytic compounds, drugs and agents as described herein.

As used herein, the term "chemopreventive" refers to any compound, drug, or agent used to prevent tumorigenesis in a subject predisposed (e.g., high risk of developing) to a particular type of cancer. Chemopreventive agents can be used in conjunction with the compounds of the present invention as described herein. A chemopreventive can also be any compound, drug, or agent that prevents recurrence of cancer once it has been irradicated from a subject.

As used herein, the term "high risk subject" refers to a subject that is predisposed to developing a particular type of cancer. In the present invention, for example, a high risk subject is a subject that has a germline, hereditary mutation in a gene (e.g., BRCA gene), the mutation of which is known to lead to tumorigenesis (e.g., breast, ovarian cancer). High-risk subjects also include subjects in remission that are at risk for recurrence of cancer.

As used herein, the term "sporadic cancer" refers to a subset or subclass of cancer in which the disease-causing mutations occur in somatic cells (e.g., not germline and hereditary). The term sporadic cancer is used to differentiate cancers occurring in people who have not inherited a mutation that confers increased susceptibility to cancer, from cancers occurring in people who are known to carry a predisposing mutation (i.e., BRCA1 mutation). Sporadic is also used to describe cancer occurring in individuals without a family history of cancer (as opposed to familial cancer). For example, cancer can be classified into two classes; sporadic and hereditary. Cancer developing in subjects who do not carry a high-risk, inherited mutation (e.g., BRCA1 mutation) is referred to as sporadic cancer. The distinction is not absolute, as genetic background may influence the likelihood of cancer even in the absence of a specific predisposing mutation. For instance, given alleles of modifying genes will determine the predisposition to sporadic cancer that any given subject has. In sporadic cancer, therefore, mutations which trigger tumorigenesis are not present in the germline cells, thus affecting only the subject, not the offspring.

As used herein, the term "adjuvant therapy" refers to a cancer treatment given after the primary treatment to increase the chances of a cure. Adjuvant therapy includes, but is not limited to, chemotherapy, radiation therapy, and/or hormone therapy. For example, if a patient undergoes surgery to remove an existing breast cancer tumor, the administration of tamoxifen following such surgery would be considered an adjuvant therapy.

As used herein, the term "adjunctive therapy" refers to cancer treatment that is used in conjunction with a primary treatment and its purpose is to assist the primary cancer treatment. Adjunctive therapies are co-administered therapies. For example, if chemotherapy is a primary therapy, then the co-administration of a SPRM with the chemotherapy would be considered an adjunctive therapy.

As used herein, the term "anti-estrogen" refers to a group of compounds, drugs, or agents that acts upon estrogens and/or their receptors. For example, an anti-estrogen can be a pure anti-estrogen that is typically a compound, drug, or agent that demonstrates antagonistic effects upon an estrogen receptor. An anti-estrogen is also a selective estrogen receptor modulator (SERM) such that a compound, drug, or agent demonstrates both antagonistic and agonistic effects upon an estrogen receptor.

As used herein, the term "anti-progesterone" refers to a group of compounds, drugs or agents that acts upon progesterone and/or its receptor. For example, an anti-progesterone can be a pure anti-progesterone that is typically a compound, drug, or agent that demonstrates antagonistic effects upon a progesterone receptor. An anti-progesterone is also a selective estrogen receptor modulator (SPRM) such that a compound, drug, or agent that demonstrates both antagonistic and agonistic effects upon an estrogen receptor. For the purposes of this application, the SPRM acronym encompassing all compounds, agents, or drugs that act upon progesterone and/or its receptor.

DETAILED DESCRIPTION OF THE INVENTION

The present invention provides methods of preventing or delaying the development of cancer (e.g., breast cancer) in BRCA1 mutation positive patients by beginning progesterone receptor antagonist treatment at an early age (e.g., by age 35, 30, or 25). In certain embodiment, such early treatment is long-term treatment, which may substitute or delay a preventative single or double mastectomy (e.g., in patients wishing to delay or avoid a mastectomy, or patients that cannot afford a mastectomy).

Cancer related diseases take many lives each year. The technology that allows diagnosticians and medical professionals to study a person's genome allows them the unique opportunity to prevent diseases before they occur, even cancer related diseases, based on a subject's genetic predisposition. Although the present invention can be used to treat cancer subjects, it also provides medical professionals the unique opportunity to prevent cancer from forming in a subject that is diagnosed as being a high risk cancer patient (e.g., one that has a genetic predisposition to a particular cancer). The present invention provides for preventing, treating, and preventing recurrence of subjects that are high risk for progesterone receptor related cancers. Typically, these high risk subjects have mutations present in BRCA1 and/or BRCA2, however it is highly probable that future discoveries will be made that identify additional mutations in other genes that will predispose a person to a progesterone receptor related cancer. These types of cancers can also be prevented and treated by the methods and compositions of the present invention. Once a genetic test has determined whether or not a subject has a genetic mutation that predisposes them to progesterone related cancer, preventative treatment can be administered as described herein.

The methods and compositions of the present invention are not limited to cancers that are genetic in origin. They are equally applicable to cancers that are somatic in origin (e.g., sporadic cancer). For example, when a patient develops a sporadic progesterone receptor related cancer, the present invention can be used to treat those subjects, either alone or in a co-therapy regimen. As well, for those subjects where a progesterone related cancer (either hereditary or sporadic) is in remission, either through chemical, radiological, or surgical means, the methods and compositions of the present invention can be administered to prevent recurrence of the related cancer. Therefore, the methods and compositions of the present invention can be used in vital ways to help prevent and/or treat those subjects who have, or might develop, cancer.

The present invention is not limited to a particular mechanism. Indeed, an understanding of the mechanism is not necessary to practice the present invention. Nonetheless, it is contemplated that increased PR expression in BRCA1$^{+/-}$ or BRCA1$^{-/-}$ epithelial cells promotes proliferation of surrounding ERα/PR-negative MECs and leads to the development of ERα/PR-negative mammary tumors. Since PR-A over-expression was shown to be carcinogenic (Shyamala, 1998), it is contemplated that BRCA1 mutations promote breast carcinogenesis in part through the accumulation and activation of PR-A, although PR-B may also have a role. An overall increase in breast cancer risk is clearly seen in menopausal progesterone-estrogen use in a large Women's Health Initiative prospective hormone replacement therapy study. The present invention is not limited to a particular mechanism. Indeed, an understanding of the mechanism is not necessary to practice the present invention. Nonetheless, it is contemplated that deregulated PR turnover defines a tissue-specific function of BRCA1 in breast epithelial cells and is consistent with the reported carcinogenic effect of progesterone.

Selective progesterone receptor modulators can be used to prevent progesterone receptor positive cancer in patients where cancer is not yet diagnosed. As well, SPRMs are useful as treatment and therapy agents in early stage progesterone related cancers, where PR is still expressed. Further, SPRMs are useful as adjuvant, maintenance therapies to prevent cancer recurrence following the primary therapy. The use of SPRMs is also contemplated for use as a co-therapy, or adjunctive therapy, with existing cancer therapeutics such as chemotherapy, radiation therapy, etc. The present invention is not limited to a particular mechanism. Indeed, an understanding of the mechanism is not necessary to practice the present invention. Nonetheless, it is contemplated that as an adjunctive therapy, the primary therapeutic treatment destroys cancer cells that do not express PR, and the SPRM targets those cells that are PR+ and are providing growth factor signals to adjacent PR− cells thereby decreasing the incidence of new tumorigenesis.

As described herein, experiments were performed to exemplify embodiments of the present invention.

Mice carrying the homozygous exon 11 floxed BRCA1 (Xu et al., 1999, Nat. Genet. 22:37) and/or exon 5 & 6 floxed p53 alleles (Lin et al., 2004, Cancer Res. 64:3525) (BRCA1$^{\Delta11}$/p53$^{\Delta5\&6}$ and p53$^{\Delta5\&6}$ hereafter) as well as a WAP-Cre$^c$ transgene were studied. The WAP-Cre$^c$ transgene is constitutively expressed in the mammary gland leading to inactivation of both BRCA1 and/or p53 alleles in the nulliparous mice, in contrast to other transgenes that require pregnancy for maximal promoter activity (Lin et al., 2004). The inactivation of BRCA1/p53 in the mouse mammary gland genetically mimics human breast carcinogenesis since the majority of BRCA1 mediated tumors in humans harbor p53 mutations (Ting et al., 2004, DNA Repair 3:935; Turner et al., 2004, Nat. Rev. Cancer 4:814). As shown in FIG. 1A, PCR analyses, using genomic DNA as templates, detected WAP-Cre$^c$ mediated deletions of p53 and BRCA1 alleles, respectively, in the mammary gland of the corresponding mice (FIG. 1A). As early as 2.5 months of age, BRCA1$^{\Delta11}$p53$^{\Delta5\&6}$ mammary glands from mature nulliparous mice showed approximately 4.9 fold more branching points than that of wild-type (wt) or p53$^{\Delta5\&6}$ gland (FIG. 1B). By 4 months, in addition to further accumulation of branches, extensive alveolar formation was noticeable in nulliparous BRCA1$^{\Delta11}$p53$^{\Delta5\&6}$ mice but not in age-matched p53$^{\Delta5\&6}$ mice (FIG. 1C).

The morphology of mature, nulliparous BRCA1$^{\Delta11}$/p53$^{\Delta5\&6}$ mammary glands is similar to that of pregnant mice suggesting that proliferation of MECs in these genetically modified mammary glands is altered. As shown in FIG. 1D, approximately 8 fold higher proliferation was detected in BRCA1$^{\Delta11}$p53$^{\Delta5\&6}$ than in wt or p53$^{\Delta5\&6}$ mammary glands at the estrous phase (FIG. 1D, P≤0.05). Proliferation in BRCA1$^{\Delta11}$p53$^{\Delta5\&6}$ mammary gland at the proestrous phase is also significantly elevated when compared with p53$^{\Delta5\&6}$ or wt mammary gland (FIG. 1D). As elaborated lateral branching and alveolar expansion in the mammary glands of pregnant mice depend on receptor activation by progesterone and other ligands, it is contemplated that deregulated nuclear receptors signaling contributes to BRCA1$^{\Delta11}$p53$^{\Delta5\&6}$ mammary gland morphology.

Figure 2:
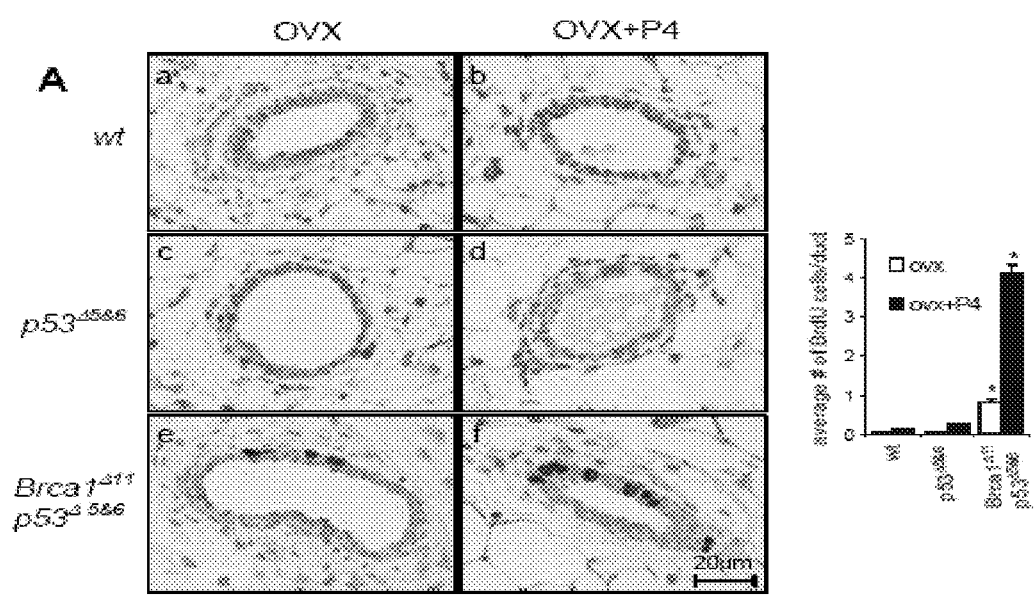
FIGS. 2A-2E show mitogenic effects of progesterone on $BRCA1^{\Delta 11/}p53^{\Delta 5 \& 6}$ mammary mammary glands and stabilization of progesterone receptor in BRCA1 epithelial cells; (A) Ovarian hormones-independent and progesterone (P4)-induced proliferation of mammary epithelial cells as measured by BrdU incorporation. Ovariectomized mice (14-20 weeks old) were treated with vehicle, or 1 mg of progesterone for 3 days and BrdU was injected 2 hr before sacrifice. BrdU-positive mammary epithelial cells (MECs) per duct were quantified in 15 mammary ducts. Control ovariectomized and progesterone (P4)-treated mice are shown. (B) Expression of PR in the mammary gland. Paraffin sections of wt (a,b), $p53^{\Delta 5 \& 6}$ (c,d) and $BRCA1^{\Delta 11/}p53^{\Delta 5 \& 6}$ (e,f) mammary glands at the proestrous or estrous phase were subjected to immunohistochemical staining for PR expression. The histogram represents the average percentage of PR expressing cells/duct. A minimum of 5 ducts per animal was evaluated. (C) Quantitative Real Time PCR was performed to measure the mRNA expression of PR-A plus PR-B (PR total) and PR-B only in $p53^{\Delta 5 \& 6}$ and $BRCA1^{\Delta 11/}p53^{\Delta 5 \& 6}$ mammary glands. (D) Effects of proteosome inhibitor, MG132, on PR protein levels in normal $p53^{\Delta 5 \& 6}$ and $BRCA1^{\Delta 11}p53^{\Delta 5 \& 6}$ MECs. Western blotting for PR was performed. β-actin serves as a loading control. (E) Half-life of PR. MECs were treated with 100 μg/ml cyclohexamide and 10 nM R5020. Cells were harvested at the indicated time points. Cell lines used: $p53^{\Delta 5 \& 6}$MECs, open circles; $BRCA1^{\Delta 11}p53^{\Delta 5 \& 6}$ MECs, closed circles.
Figure 2:
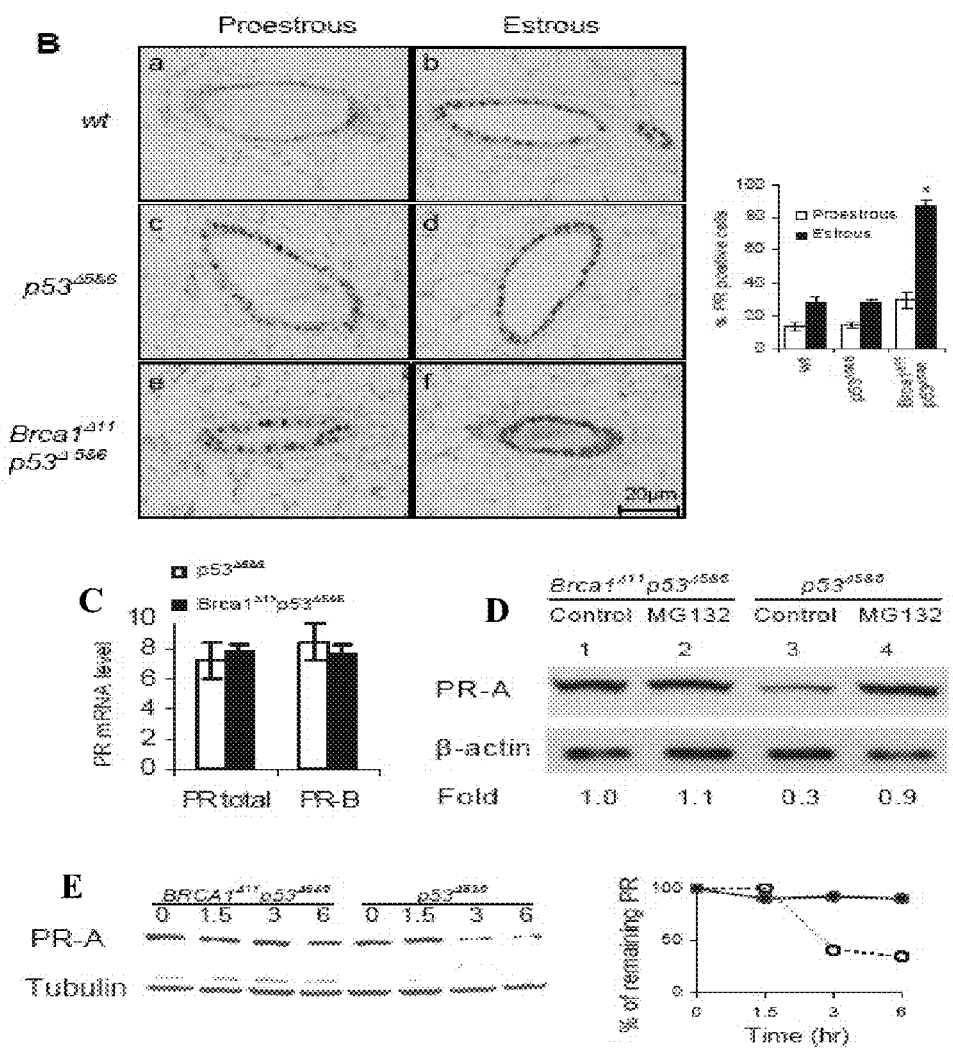

MEC proliferation peaks at the estrous phase when progesterone level is highly elevated. To assess the contribution of steroid hormones to MECs proliferation an ovariectomy was performed to deplete circulating estrogen and progesterone. Since PR is one of the downstream target genes of ER, progesterone activity was targeted. Two weeks after ovariectomy mice were treated with progesterone daily for 3 days followed by BrdU pulse labeling. In control vehicle treated mice, no BrdU-positive MECs were found in ovariectomized wt, and p53$^{\Delta5\&6}$ gland, but ducts containing one or two BrdU-positive cells were detected in BRCA1$^{\Delta11}$p53$^{\Delta5\&6}$ mammary glands (FIG. 2A). Elevated proliferation seen under ovarian hormone depletion is related to the ligand-independent activation of PR in BRCA1-deficient cells. Importantly, a higher number of BrdU-positive MECs was found in BRCA1$^{\Delta11}$p53$^{\Delta5\&6}$ mammary glands upon exposure to progesterone; ducts containing up to 6 BrdU-positive cells were identified (FIG. 2A). The majority of MECs in wt or p53$^{\Delta5\&6}$ mammary gland of progesterone treated mice did not contain BrdU-positive cells; this is consistent with the notion that progesterone alone is a weak mitogen for MECs (Clark et al., 2003, Steroids 68:789). Since PR is one of the target genes of ER, exposure to estradiol also promoted proliferation of BRCA1$^{\Delta11}$p53$^{\Delta5\&6}$ MECs as expected. Increased proliferation in BRCA1$^{\Delta11}$p53$^{\Delta5\&6}$ MECs upon progesterone exposure shows that PR activity is upregulated.

Figure 6:
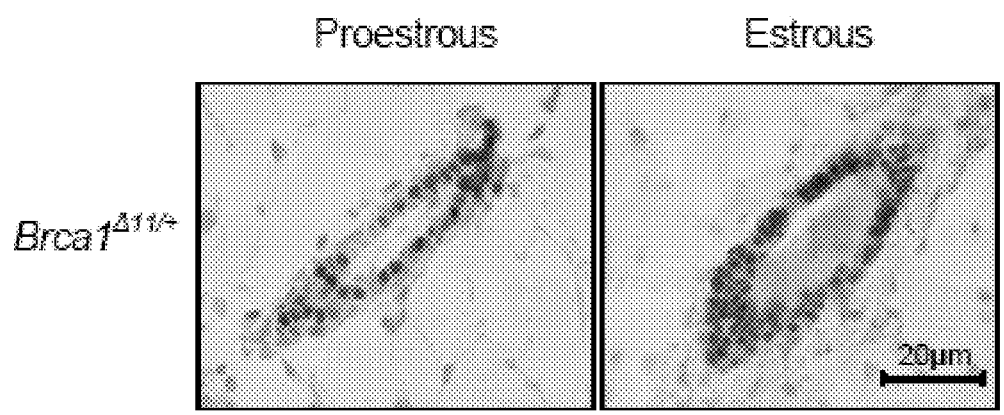
FIG. 6 shows elevated PR expression in heterozygous $BRCA1^{\Delta 11/+}$ mice. Mammary gland sections of $BRCA1^{\Delta 11/+}$ mice at the proestrous or estrous phase were subjected to immunohistochemical staining for PR expression.
Figure 7:
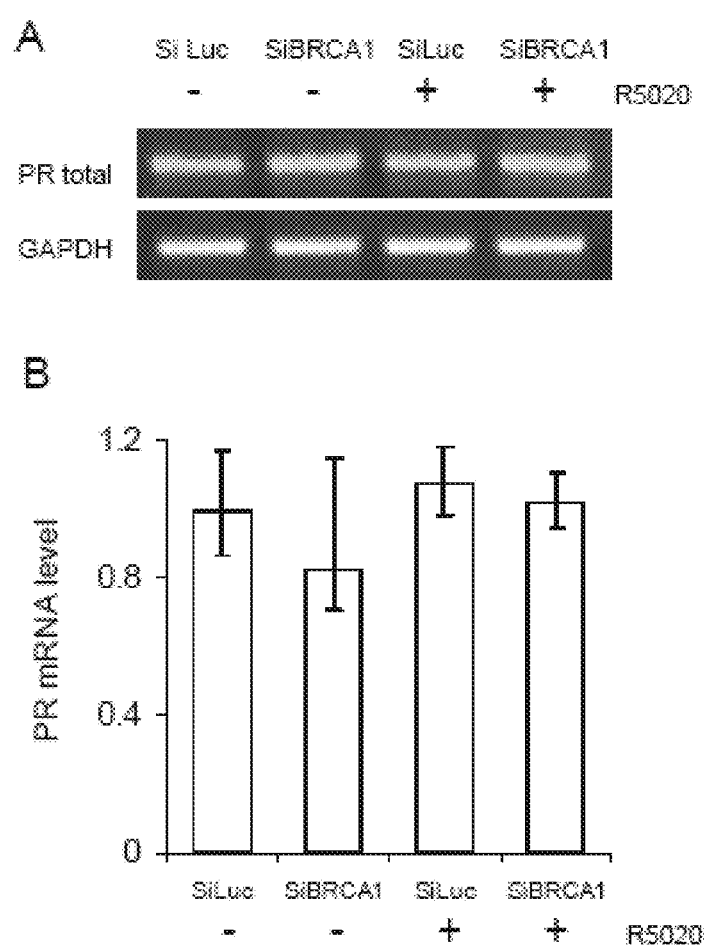
FIGS. 7A and 7B show PR-B mRNA or total PR mRNA transcripts in human breast cancer cells T47D with BRCA1 knockdown. PR mRNA was quantified in human breast cancer cells T47D with BRCA1 or control luciferase siRNA knockdown.

To demonstrate further, PR mRNA was analyzed by quantitative real time PCR. There was no significant difference in both PR-B mRNA and total PR mRNA levels at the estrous phase in mice of different genotypes (FIG. 2C). Similar results were obtained in the human breast cancer cell line T47D when comparing to control cells and BRCA1 knockdown cells by siRNA (FIG. 7). Next, PR protein expression was analyzed in the individual MEC using immunohistochemical approaches. At the proestrous phase nuclear PR was detected in a scattered subset of epithelial cells; no significant differences were detected in the percentage of PR-positive MECs in mice of all genotypes (FIG. 2B). At the estrous phase PR expression was detected in 86.8±4.0% of BRCA1$^{\Delta11}$p53$^{\Delta5\&6}$ MECs, significantly higher when compared with 27.8±3.4% and 28.2±2.4% MECs in wt or p53$^{\Delta5\&6}$ mammary gland, respectively (FIG. 2B). The staining pattern of PR in BRCA1$^{\Delta11/+}$ MECs was similar to that of BRCA1$^{\Delta11}$p53$^{\Delta5\&6}$ MECs, demonstrating that BRCA1 deficiency is directly correlated with PR accumulation (FIG. 6). This is consistent with the observation in human BRCA1 carriers (King et al., 2004). Thus, BRCA1 regulates PR at the post-transcriptional level.

MEC cultures from BRCA1$^{\Delta 11}$p53$^{\Delta 5\&6}$ and p53$^{\Delta 5\&6}$ mammary glands of two-month-old mice when MECs are histologically normal were created. The amount of PR protein, determined by western blotting, was 3-fold higher in BRCA1$^{\Delta 11}$p53$^{\Delta 5\&6}$ than in p53$^{\Delta 5\&6}$ MECs (FIG. 2D, lanes 1, 3). To further establish that PR protein stability is modulated by a proteasome pathway, MECs were exposing to MG132. PR-A was stabilized in p53$^{\Delta 5\&6}$ but not in BRCA1$^{\Delta 11}$p53$^{\Delta 5\&6}$ MECs (FIG. 2D, lanes 2, 4). In the presence of synthetic progesterone, R5020, the half-life of PR-A was 2.8 hr in p53$^{\Delta 5\&6}$ MECs; while 90% of PR-A were present at 6 hr post R5020 treatment in BRCA1$^{\Delta 11}$p53$^{\Delta 5\&6}$ MECs (FIG. 2E). These results demonstrate that the turnover rate of PR is much slower in BRCA1-deficient MECs that eventually leads to PR accumulation.

Figure 3:
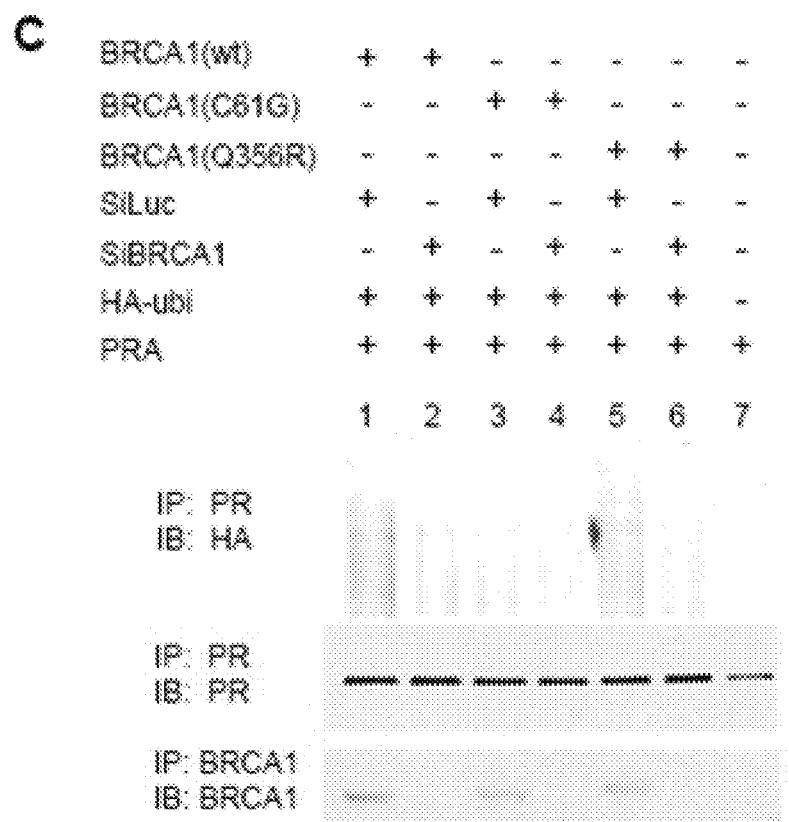
FIGS. 3A-3C show the effects of BRCA1 knockdown on PR stability and PR polyubiquitination in human breast epithelial cells. (A) PR-B and PR-A but not ERα levels are regulated by BRCA1. The human breast cancer cell line T47D was infected with siLuc or siBRCA1 adenovirus, levels of ERα and PR protein were compared using western blotting in the presence or absence of R5020 ligand and MG132. Alpha-tubulin serves as a loading control. (B) BRCA1 regulates PR ubiquitination in vivo. MCF10A cells were transiently co-transfected with HA-tagged ubiquitin, PR-A, and BRCA1 constructs (wt or mutants) as indicated, followed by infection with adenovirus that expresses siRNA targeting BRCA1 or luciferase (Luc). Before harvest, cells were treated with 10 µM MG132 for 2 hr, followed by incubation with 10 nM R5020 for 2 hr. Immunoprecipitates (IP) with PR antibodies were analyzed by immunoblotting (IB) using HA (top), and PR (middle) antibodies. Anti-BRCA1 immunoblotting shows the effects of siBRCA1 (bottom). (C) Requirement of Ring, but not Rad50 interacting domain of BRCA1 in PR ubiquitination. MCF10A cells were transfected with wt or mutant BRCA1 as indicated. In vivo ubiquitination of PR was analyzed as described in B.
Figure 8:
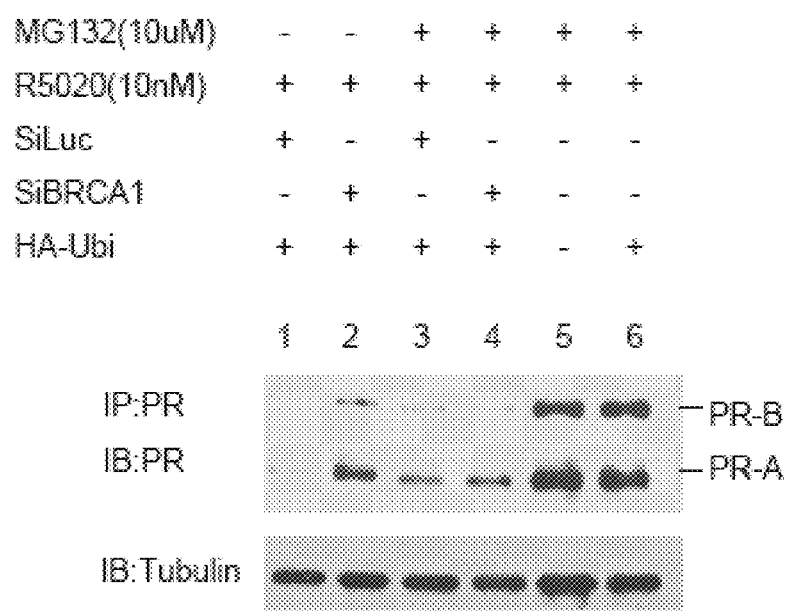
FIG. 8 shows increased PR-B and PR-A protein levels in T47D cells with BRCA1 knockdown. Immunoprecipitation followed by western blotting was carried out to detect PR-A and PR-B protein.

To further test whether BRCA1 specifically affects PR stability, adenoviral siRNA-mediated knockdown of BRCA1 was introduced to T47D cells. BRCA1 knockdown resulted in a three fold increase in PR-A protein amount, but did not affect ERα levels (FIG. 3A, lanes 1,2). Treatment with MG132 significantly stabilized PR-A in control siLuc infected cells (FIG. 3A, lane 1 vs 3, density 1.0 vs 3.8), but not in siBRCA1 infected cells (FIG. 3A, lane 2 vs 4, density 3.2 vs 3.6). In contrast to PR-A, ERα was stabilized to a similar extent in either siLuc or siBRCA1 knockdown cells treated with MG132 (FIG. 3A upper panel). In the absence of a ligand, PR-A was very stable and no significant differences were detected between siLuc and siBRCA1 knockdown cells (FIG. 3A, lanes 5, 6). The amount of PR-B was analyzed by immunoprecipitation followed by western blot (FIG. 8). Depletion of BRCA1 by adenoviral siRNA led to PR-A and PR-B accumulation. Further treatment with MG132 did not affect their stability (FIG. 8). Collectively, this demonstrates that BRCA1 regulates ligand-dependent turnover of PR-A and PR-B through proteasome degradation.

To demonstrate that ligand-induced polyubiquitination of PR is regulated by BRCA1, BRCA1 depleted human breast epithelial cells MCF10A were transfected with PR-A and HA-ubiquitin expression plasmids. As shown in FIG. 3B (lanes 1, 2), PR polyubiquitination was abrogated in BRCA1-depleted cells when compared with siLuc adenovirus infected cells. Consistent with a role of BRCA1 in PR polyubiquitination, over-expression of wt BRCA1 significantly increased the amount of ubiquitinated PR (FIG. 3B, lane 3). Since the ring domain of BRCA1 is essential for its E3 ubiquitin ligase activity in vitro, it was tested whether PR polyubiquitination is mediated by the E3 ligase activity of BRCA1. Wt, ubiquitin ligase-defective ring-domain mutant BRCA1$^{C61G}$ (Hashizume et al., 2001, J. Biol. Chem. 276: 14537), and Rad50 interaction-defective mutant BRCA1$^{Q356R}$ (Furuta, 2005) were introduced into MCF10A cells, respectively. The amount of polyubiquitinated PR-A increased in cells over-expressing wt, and BRCA1$^{Q356R}$, but not BRCA1$^{C61G}$ (FIG. 3C). Therefore, the ring domain of BRCA1 is required for PR polyubiquitination. An in vitro ubiquitination assay was performed to test whether PR-A is a substrate of BRCA1-BARD1 E3 ligase complex.

Figure 9:
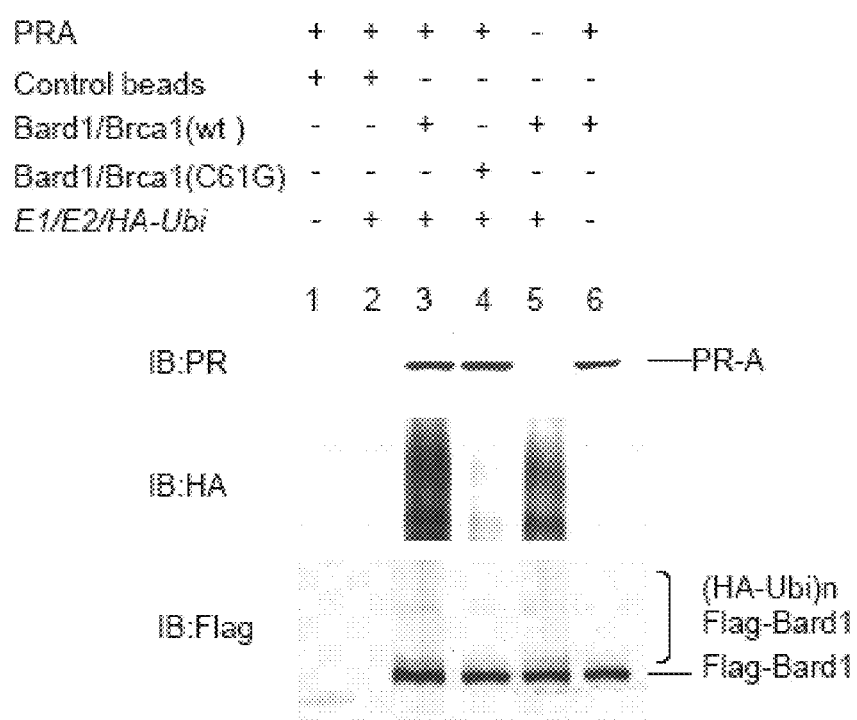
FIG. 9 shows that the BRCA1/BARD1 complex does not ubiquitinate PR-A in vitro. PR protein was phosphorylated using extract of HeLa cells (pretreated with EGF) and prebound to BRCA1/BARD1 complex (wt or C61G mutant) immobilized to protein A beads with anti-Flag antibody (lanes 3-6). In lanes 1 and 2, protein A beads without bound BRCA1/BARD1 were used as negative control beads. After washing to remove nonspecific bound proteins, the ubiquitination reaction was carried out in the presence of HA-ubiquitin, ATP, E1, and E2 as indicated. Reactions were terminated and proteins separated by SDS-PAGE and analyzed by immunoblotting with anti-PR (top) and anti-HA (middle) antibodies, respectively. Aliquots of the reaction mixture were analyzed by Flag antibody to detect BARD1 and ubiquitinated BARD1 (bottom).

While BARD1 was auto-ubiquitinated by BRCA1$^{wt}$-BARD1 but not BRCA1$^{C61G}$-BARD1, the complex failed to ubiquitinate PR-A although PR-A bound to both BRCA1$^{wt}$-BARD1 and BRCA1$^{C61G}$-BARD1 complex (FIG. 9, lanes 3, 4). Thus, the ring domain of BRCA1 is required for PR turnover, but the BRCA1-BARD1 complex failed to directly polyubiquitinate PR. The BRCA1-BARD1 ubiquitin ligase appears to catalyze an unusual polyubiquitination reaction through the K6 residue of ubiquitin (Wu-Baer et al., 2003, J. Biol. Chem. 278:34743; Nishikawa et al, 2004, J. Biol. Chem. 279:3916), a modification that may not lead to proteasome degradation. Thus, it is demonstrated that BRCA1 promotes ligand-induced polyubiquitination and degradation of PR indirectly.

Figure 4:
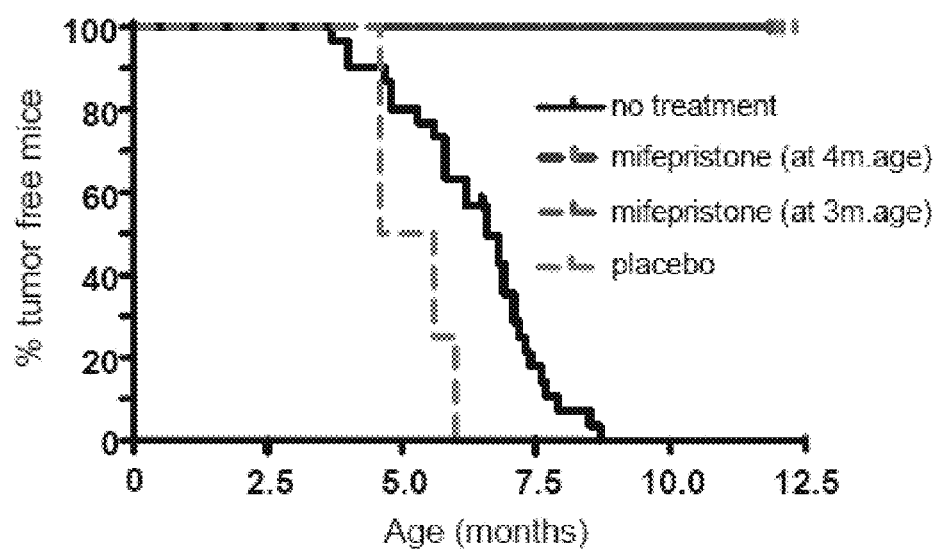
FIGS. 4A-4C show that anti-progesterone treatment inhibits mammary tumorigenesis in $BRCA1^{\Delta 11/}p53^{\Delta 5\&6}$ mice by decreasing ductal branching and alveolar proliferation. (A) Nulliparous adult female $BRCA1^{\Delta 11/}p53^{\Delta 5\&6}$ mice, age 3-4 months were implanted with either a pellet containing 35 mg/60-day constant release of mifepristone (n=14) or a placebo pellet (n=4). Mice were monitored weekly for tumor formation. (B) Mammary gland branching in control pellet (a) or mifepristone treated (b) $BRCA1^{\Delta 11}p53^{\Delta 5\&6}Cre^c$ mice. Mammary glands were removed 5 wks post pellet implantation. (C) Whole mounts of mammary glands from age-matched $BRCA1^{\Delta 11/}p53^{\Delta 5\&6}$ mice without (a, c) or with mifepristone pellet (b, d) implantation. Mammary glands were removed 5 wks post pellet implantation. LacZ staining indicates cells with an active Cre transgene.
Figure 4:
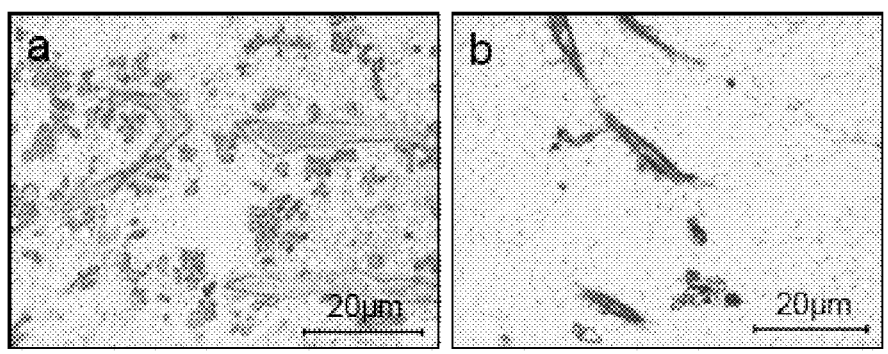
Figure 4:
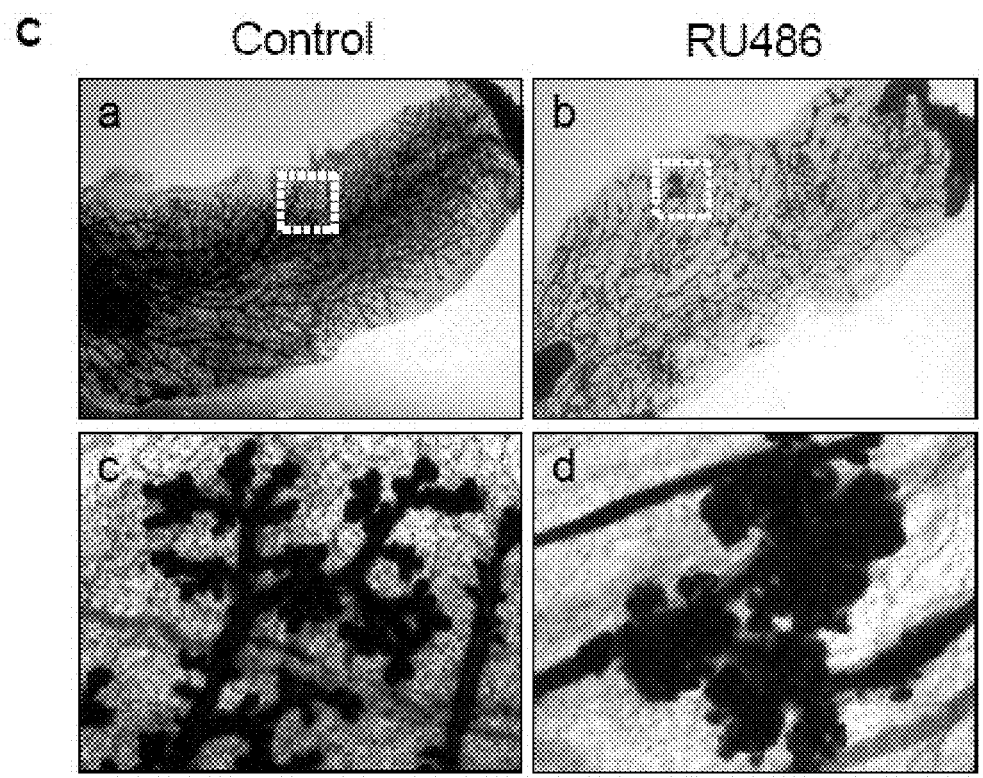
Figure 5:
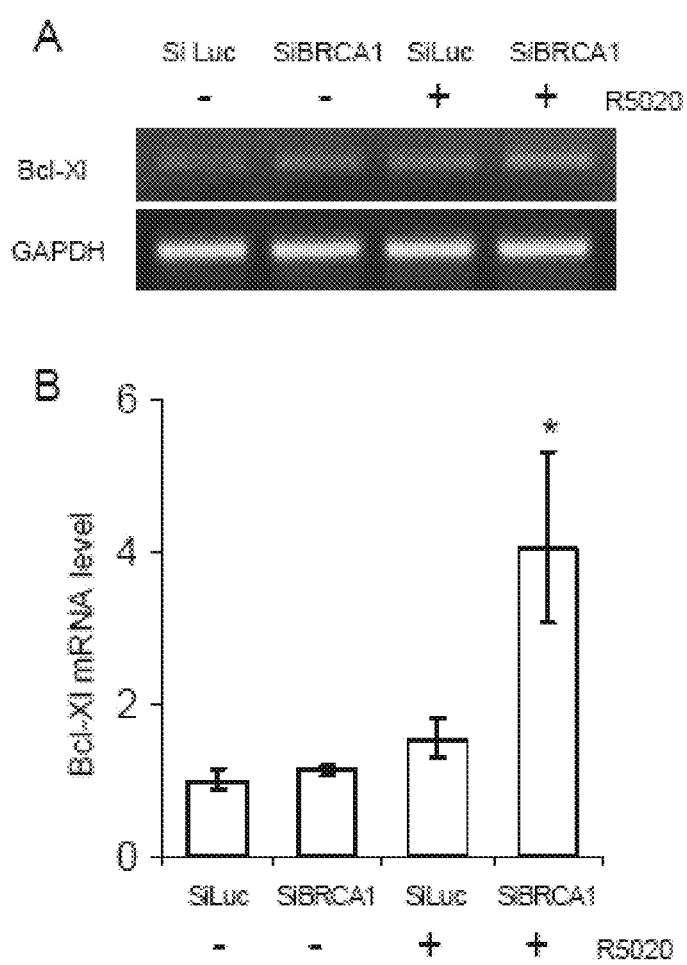
FIGS. 5A and 5B show increased expression of PR target genes in BRCA1-mutated cells. Quantitative Real Time PCR of Bcl-xl mRNA, normalized to GAPDH mRNA expression.
Figure 11:
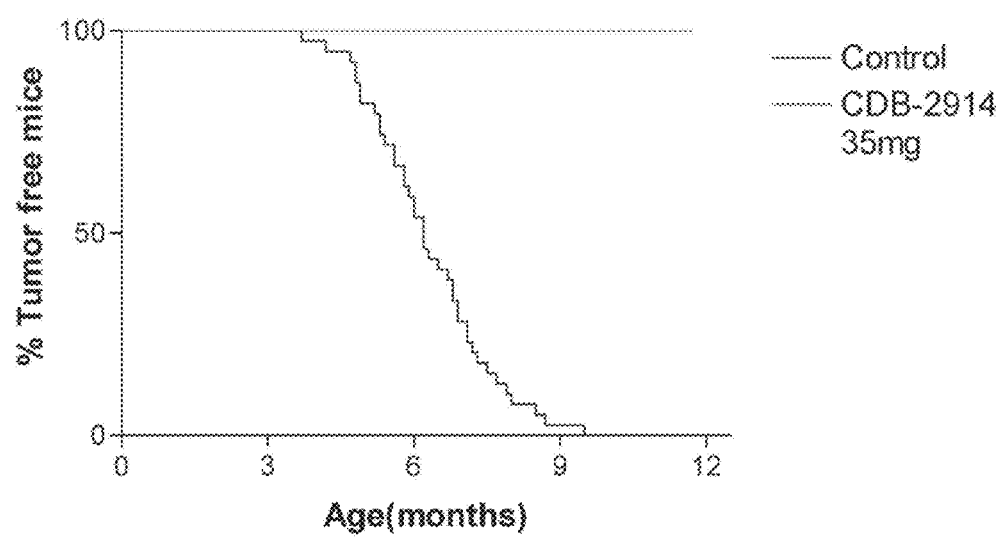
FIG. 11 demonstrates that the administration of the anti-progesterone CDB-2914 inhibits mammary tumorigenesis in mice in vivo. Nulliparous BRCA1/p53 deficient mice (ages 14 weeks) were implanted with 35 mg/60 days constant-release CDB-2914 (n=4). The control group (n=39) demonstrated a mean tumor latency of around 6 months. Mice were monitored weekly for tumor formation (p=0.0002).

As progesterone is a potent mitogen for BRCA1$^{\Delta 11}$p53$^{\Delta 5\&6}$ MECs specifically it was tested whether blocking PR signaling by anti-progesterone will prevent or delay mammary carcinogenesis in BRCA1$^{\Delta 11}$p53$^{\Delta 5\&6}$ conditional knockout mice. An anti-progesterone pellet containing 35 mg/60 days constant release mifepristone or placebo pellet was implanted into twelve 3- and two 4-month-old mice. Mice were monitored weekly for tumor formation. The median tumor latency of BRCA1$^{\Delta 11}$p53$^{\Delta 5\&6}$ conditional knockout mice was 6.6 months (n=25) with complete penetrance (FIG. 4A). All control mice or placebo pellet treated mice developed palpable tumor by 8.7 or 5.2 months of ages (n=4), respectively. In the treated group no palpable tumors were detected at 12 months of age (n=14) (FIG. 4A). The effects of on ductal branching and alveolar expansion were determined using mammary gland whole mounts and histological sections. Five weeks of treatment resulted in a substantial reduction of side branches of BRCA1$^{\Delta 11}$p53$^{\Delta 5\&6}$ mammary glands (FIG. 4B). Only 33±7 ducts in an approximate area of 0.012 mm$^2$ were identified in-treated mice while 678±49 ducts were found in placebo pellet-treated mice. Dramatic inhibition of tumorigenesis was also seen with the implantation of 35 mg time release (60 day) pellets of CDB-2914. The release of CDB-2914 in mice effectively inhibited tumors (100%) when compared to control implants (FIG. 11). As exemplified herein, CDB-2914 is also effective in delaying mammary tumors in BRCA1/p53 deficient mice over the time period tested. CDB-2914 shares structural similarity with mifepristone and binds competitively to PR with high affinity. CDB-2914 moreover possesses anti-glucorcorticoid and anti-androgen properties.

Despite the dramatic reduction in both lateral branches and alveoli upon treatment, the overall mammary gland structure was preserved (FIG. 4C, b). Using R26R reporter mice to monitor Cre activity (Soriano, 1999), LacZ-positive normal MECs were found as well as hyperplastic foci in the treated mice (FIG. 4C, b, d). These foci did not progress to tumors. Immunostaining with an antibody against cleaved caspase 3 revealed few apoptotic cells in treated mammary glands 3 wk or 5 wk post pellet implantation. Collectively, these results demonstrate that PR function is critical for BRCA1-mediated mammary carcinogenesis, and anti-progesterone treatment prevents mammary carcinogenesis. On the contrary, treatment of BRCA1$^{\Delta 11/\Delta 11}$p53$^{+/-}$ MMTV-Cre mice with tamoxifen increased mammary tumor incidence that were linked to the estrogenic activities of tamoxifen in BRCA1-deficient cells (Jones et al., 2005, Oncogene 24:3554).

Figure 10:
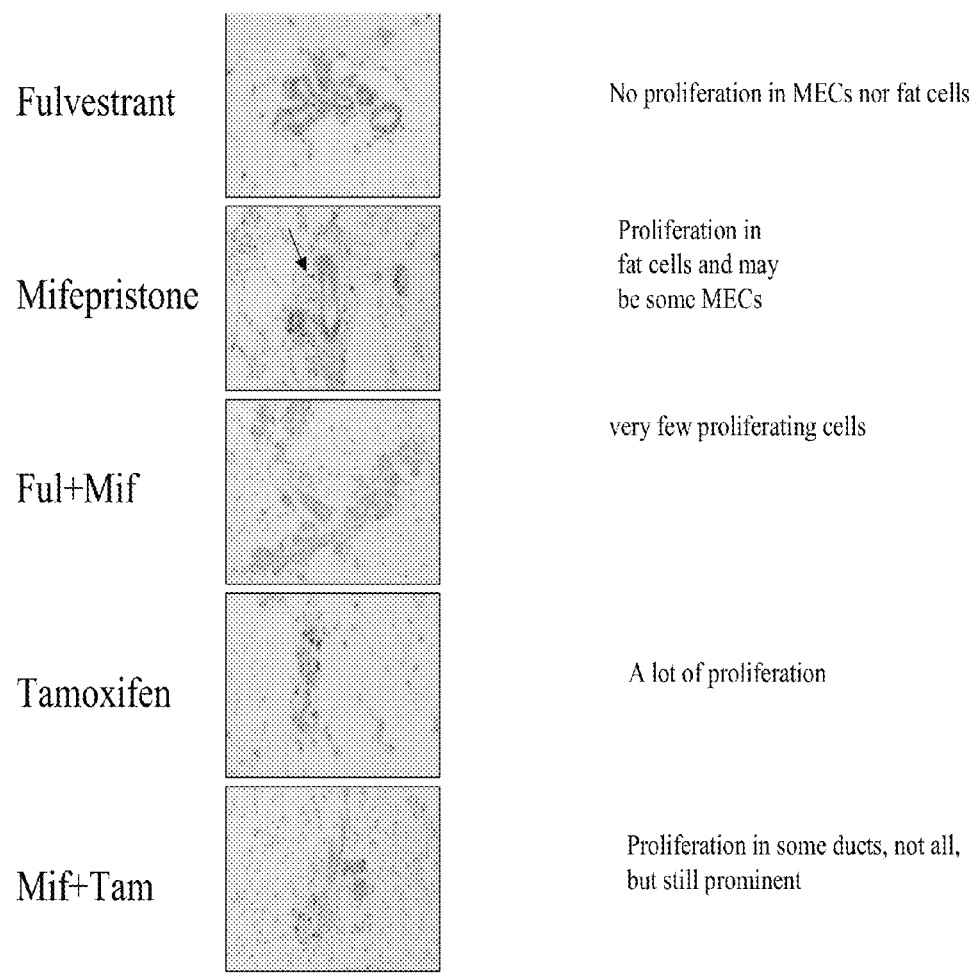
FIG. 10 shows that the combination of the anti-estrogen fulvestrant and the SPRM mifepristone inhibits proliferation of cancer cells in murine MECs. The inhibition of cancer cell proliferation is also seen with the combination of mifepristone and the anti-estrogen tamoxifen. Pictures are representative of treatment in three to four month old $BRCA1^{\Delta 11/}p53^{\Delta 5\&6}$ mice.

When combinations of the anti-estrogens tamoxifen and fulvestrant with mifepristone were injected into BRCA1Δ11/p53$^{\Delta 5\&6}$ and p53$^{\Delta 5\&6}$/p53$^{\Delta 5\&6}$ mice, proliferation of cancerous cells was greatly inhibited (FIG. 10). The combination of mifepristone and fulvestrant inhibited cell proliferation to a greater extent than did the combination of mifepristone and tamoxifen.

In one embodiment, the present invention relates to methods and compositions for preventing progesterone receptor related cancers. In some embodiments, the present invention relates to the administration of a progesterone receptor antagonist to a subject that is deemed high risk for developing a PR related cancer. In some embodiments, a selective progesterone receptor modulator or analog thereof is administered to a subject that is deemed high risk for developing a PR related cancer. In some embodiments, the PR antagonist is a small molecule drug, a nucleic acid molecule (e.g., interfering RNA), or an antibody that binds the PR as described herein. In some embodiments, a high-risk subject is a subject with a hereditary (e.g., germline) mutation known to have a high risk cancer profile. In some embodiments, a high-risk subject is a subject that has a mutation in the BRCA gene. In some embodiments, the BRCA mutation is found in the BRCA1 gene. In some embodiments, the BRCA mutation is found in the BRCA2 gene. In some embodiments, the subject is high risk for developing breast cancer, whereas in some embodiments the subject is high risk for developing ovarian cancer. In some embodiments, the high-risk subject has not been diagnosed with a cancer, but is genetically predisposed.

In one embodiment, the subject with a high risk of developing a PR related cancer is given a progesterone antagonist (e.g., mifepristone, onapristone ZK 98.299, ORG 1710, ZK 230211, ICI-182,780). In some embodiments, the subject with a high risk of developing a PR related cancer is given a selective progesterone receptor modulator. In some embodiments, the SPRM is, for example, mifepristone (RU-486 or analogs thereof such as 11β-(4-dimethylaminophenyl)-17β1-hydroxy-17α-(e-methyl-1-butynyl)-4,9-estradien-3-one and 11β-(4-acetophenyl)-17β1-hydroxy-17α-(3-methyl-1-butynyl)-4,9-estradien-3-one (Hazra et al., 2000, Steroids 65:157)), CDB-2914 also known as 17α-acetoxy-11(3-(4-N,N-dimethylaminophenyl)-19-norpregna-4,9-diene-3,20-dione) (U.S. Pat. No. 7,196,074; Rao et al, 2000, Steroids 65:395-400; Qin et al 2006, Hum. Repro. 21:2408-16; Qin et al., 2005, J. Clin. Endo. & Metab. 90:2408-16), JNJ 1250132 (Allan 2006), 3,3-disubstituted-5-aryloxindole (Fensome et al., 2002, Bio. Med. Chem. Lett. 12:3487), or 6-aryl-1,3-dihydrobenzimidazol (Terefenko et al., 2005, Bio. Med. Chem. Lett. 15:3600), asoprisnil and ORG 33628 (Chabbert-Buffet, 2005), CP8816 and CP8863 (Kurata et al., 2005, J. Pharmacol. Exp. Ther. 313:916-20), CP8668 (Tabata et al., 2003, Eur. J. Pharmacol. 461:73-8), all references are incorporated herein in their entireties. In some embodiments, the mifepristone, analog thereof, or other SPRM is given alone, whereas in some embodiments the mifepristone, analog thereof, or other SPRM is an adjunctive therapy with one or more additional preventive therapies. Additional preventive therapies include, but are not limited to, chemopreventive drugs such as anti-estrogens (e.g., fulvestrant (Dowsett et al., 2005, Breast Cancer Res. Treat. 93:11-18, also known as Faslodex™ and ICI-182780), EM-652 and EM-800 (Labrie et al., 1999, J. Steroid. Biochem. Mol. Biol. 69:51-84), tamoxifen, reloxifene, toremifen), aromatase inhibitors (e.g., anastrozole, exemestane, letrozole), vitamin A (e.g., natural or synthetic), phytoestrogens (e.g., found in flaxseed). It is contemplated that the present invention is not limited to the type of SPRM and/or anti-estrogens used, indeed many SPRMs and anti-estrogens and analogs thereof are available and known to those skilled in the art and are equally applicable in methods of the present invention.

In one embodiment, the PR antagonist is administered to a subject that has been newly diagnosed with a progesterone receptor related cancer. In some embodiments, the PR antagonist is an antibody that binds to the PR as described herein. In some embodiments, the PR antagonist is a SPRM. In some embodiments, the PR related cancer is breast cancer or ovarian cancer. In some embodiments, the PR related cancer is caused by mutations in either the BRCA1 or the BRCA2 gene. In some embodiments, the cancer is a sporadic cancer in that it is not hereditary or germline derived, however the cancer is still PR related. In some embodiments, the SPRM is administered alone, whereas in other embodiments the SPRM is administered as an adjuvant or adjunctive therapy with another drug, compound, or procedure (e.g., surgery) useful in treating the cancer as described herein. In some embodiments the SPRM is mifepristone or an analog thereof as described herein. In some embodiments, the SPRM is administered as an adjuvant or adjunctive therapy with an anti-estrogen (e.g., fulvestrant, tamoxifen, reloxifene, toremifene). In some embodiments the SPRM is administered as an adjuvant or adjunctive therapy with an aromatase inhibitor (e.g., anastrozole, exemestane, letrozole).

In one embodiment, a subject is administered an antagonist against the steroid receptor co-activator protein 3. In some embodiments, the antagonist is a compound drug or agent. In some embodiments, the antagonist is an antibody that binds to the SRC3 protein. In some embodiments, the SRC3 antagonist is administered as an adjuvant or adjunctive therapy with a SPRM, anti-estrogen, and/or aromatase inhibitor.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002, incorporated herein in its entirety.

In some embodiments the present invention provides methods of storage and administration of the antagonist, agent, compound, or drug in a suitable environment (e.g. buffer system, adjuvants, etc.) in order to maintain the efficacy and potency of the agent, compound, or drug such that its usefulness in a method of treatment of a cancer as described herein is maximized. For example, protein agents, chemicals or nucleic acids benefit from a storage environment free of proteinases and other enzymes or compounds that could cause degradation of the protein, chemical, or nucleic acid.

A preferred embodiment is contemplated where the antagonist, agent, compound, or drug is administered to the individual as part of a pharmaceutical or physiological composition for treating a PR related cancer. Such a composition can comprise an antagonist and a physiologically acceptable carrier. Pharmaceutical compositions for co-therapy can further comprise one or more additional therapeutic agents. The formulation of a pharmaceutical composition can vary according to the route of administration selected (e.g., solution, emulsion, capsule). Suitable pharmaceutical carriers can contain inert ingredients that do not interact with the PR antagonist function and/or additional therapeutic agent(s). Standard pharmaceutical formulation techniques can be employed, such as those described in Remington's Pharmaceutical Sciences, Mack Publishing Company, Easton, Pa. Suitable physiological carriers for parenteral administration include, for example, sterile water, physiological saline, bacteriostatic saline (saline containing about 0.9% benzyl alcohol), phosphate-buffered saline, Hank's solution, Ringer's-lactate and the like. Methods for encapsulating compositions (such as in a coating of hard gelatin or cyclodextran) are known in the art (Baker, et al, "Controlled Release of Biological Active Agents", John Wiley and Sons, 1986). The particular co-therapeutic agent selected for administration with a PR antagonist will depend on the type and severity of the cancer being treated as well as the characteristics of the individual, such as general health, age, sex, body weight and tolerance to drugs.

In some embodiments the therapeutic agent is administered by any suitable route, including, for example, orally (e.g., in capsules, suspensions or tablets) or by parenteral administration. Parenteral administration can include, for example, intramuscular, intravenous, intra-articular, subcutaneous, or intra-peritoneal administration. In some embodiments, the method of administration of the therapeutic agent is by direct injection into, or adjacent to, the tumor. The therapeutic agent can also be administered transdermally, topically, by inhalation (e.g., intra-bronchial, intra-nasal, oral inhalation or intra-nasal drops) or rectally. Administration can be local or systemic as indicated. The preferred mode of administration can vary depending upon the particular agent chosen. A timed-release, subcutaneous mode of administration is also contemplated. For example, a therapeutic agent is inserted under the skin either by injection, and/or by placing a solid support that has been previously impregnated or which contains (e.g., a capsule) the therapeutic agent, under the skin. An effective amount of the therapeutic agent is then released over time (e.g., days, weeks, months, and the like) such that the subject is not required to have a therapeutic agent administered on a daily basis.

In some embodiments, a therapeutically effective amount of a SPRM and/or anti-estrogen to be administered to a subject is at least 30 mg per diem (e.g, 30 mg . . . 35 mg . . . 40 . . . 45 . . . 50 . . . or 75 mg per diem, or between 30-50 mg per diem). In some embodiments, a therapeutically effective amount of a SPRM and/or anti-estrogen to be administered to a subject is at least 35 mg per diem. In some embodiments, a therapeutically effective amount of a SPRM and/or anti-estrogen to be administered to a subject is at least 50 mg per diem per SPRM and/or anti-estrogen. In some embodiments, the effective amount is at least 100 mg per diem. In further embodiments, the effective amount given to a subject is at least 150 mg, at least 200 mg, at least 300 mg, at least 400 mg, or at least 500 mg per diem. In preferred embodiments, the effective amount of a SPRM and/or anti-estrogen to be administered to a subject at high risk of developing cancer or to a subject with a high-risk cancer is at least 200 mg per diem.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers and are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In some embodiments, the administration of a SPRM and/or anti-estrogen to a subject is time-released. For example, the SPRM and/or anti-estrogen is administered to a subject in such a way (e.g., tablets, capsules, impregnated skin patch, etc.) that the composition is effectively administered to a patient over a period of 1 hour, 1 day, 10 days, 20 days, 30 days, 60 days, etc.

When co-administration of a PR antagonistic therapeutic agent and an additional therapeutic agent is indicated or desired for treating a subject having a PR related cancer, the antagonistic therapeutic agent can be administered prior to, concurrently with, or subsequent to administration of the additional therapeutic agent. When the antagonistic therapeutic agent and the additional therapeutic agent are administered at different times, they are preferably administered within a suitable time period to provide substantial overlap of the pharmacological activity of the agents. The treating physician will be able to determine the appropriate timing for co-administration of antagonistic therapeutic agents and an additional therapeutic agent.

The present invention provides isolated antibodies. In preferred embodiments, the present invention provides monoclonal antibodies that specifically bind to an isolated polypeptide comprised of at least five amino acid residues of PR antigens (e.g., Genbank Accession No. NP_000917). These antibodies find use in the therapeutic methods described herein.

The following examples are provided in order to demonstrate and further illustrate certain preferred embodiments and aspects of the present invention and are not to be construed as limiting the scope thereof.

Example 1

Animals and Genotyping

The p53$^{f5\&6/f5\&6}$ WAP-Cre$^c$ mice were generated for somatic inactivation of p53 in mammary epithelial cells as described by Lin et al., 2004, Cancer Res. 64:3525. By breeding with mice harboring two exon 11 floxed BRCA1 alleles (obtained from NIH, NCl mouse repository), compound transgenic mice were generated. Mice were in a C57BL/6 and 129/Sv mixed background, or BALB/c and C57BL/6 mixed background. The presence of floxed, deleted p53 and BRCA1 alleles, and Cre recombinase were determined using polymerase chain reaction (PCR) with toe DNA as template. Rosa26-LacZ reporter, R26R (Soriano, 1999, Nat, Genet. 21:70) was used to monitor Cre-active cells in the mammary gland. Mice were maintained in accordance with regulation of Institutional Animal Care and Use Committee of University of California, Irvine.

Example 2

Estrous Stage Determination

Stages of estrous were determined by cytological evaluation of vaginal smears as described in Inderdeo et al., 1996, Biol. Reprod. 55:498. Vaginal smears of adult female nulliparous mice age 10-14 wk were taken once a day at noon. Mice were monitored for at least one estrous cycle and only mice undergoing normal estrous cycle were used for further experiments. After determining the estrous stage mice were injected intraperitoneally with 50 µg of 5-bromo-2-deoxyuridine (BrdU; Sigma, St. Louis, Mo.) per gram of body weight and sacrificed two hr later. Mammary glands were isolated and processed for immunohistological analysis as previously described in Lin et al., 2004, Cancer Res. 64:3525.

Example 3

Histology and Immunohistochemistry

Mammary glands were collected, fixed in 4% paraformaldehyde and processed through paraffin embedding. Sections were cut 5 µm thick and subjected to immunohistochemical analysis. Immunostaining was performed as described in Vectastain Elite ABC kit (Vector Laboratories, Burlingame, Calif.). Antibodies used for immunostaining were: BrdU (mouse monoclonal biotinylated, ZBU30, Zymed, San Francisco, Calif., dilution 1:100), PR antibody (rabbit polyclonal, C-19, sc-538, Santa Cruz Biotechnology, Santa Cruz, Calif.; dilution 1:2000), ERα (MC-20, sc-542, Santa Cruz Biotechnology, Santa Cruz, Calif.; dilution 1:2000).

Example 4

Mammary Gland Whole Mount

The mammary gland was removed and flattened on paraffin paper and fixed in Carnoy's fixative (60% of absolute ethanol, 30% CHCl$_3$, 10% HOAc) for 3 hr. It was subsequently hydrated through a series of solutions with decreasing concentrations of ethanol, and stained in carmine solution (1 g carmine, 2.5 g aluminum potassium sulfate/500 ml of water) overnight. The gland was dehydrated through a series of solutions with increasing ethanol concentrations, 50-100%, washed in xylene twice, and mounted on a slide.

Example 5

X-Gal Staining

The whole mammary gland was spread and fixed for 1-2 hr in 2% paraformaldehyde, 0.25% glutaraldehyde, 0.01% NP40 in PBS. After fixation, the mammary gland was rinsed in PBS and incubated for 2 hr. in a buffer containing 2 mM MgCl$_2$, 0.01% Na-deoxycholate, and 0.02% NP-40 in PBS Staining was performed by incubating the gland at 30° C. for 16-24 hours in staining buffer (5 mM K$_4$Fe(CN)$_6$3H20, 5 mM K$_3$Fe(CN)$_6$, 2 mM MgCl$_2$, 0.01% Na-deoxycholate, 0.02% NP-40 in PBS) followed by rinsing in PBS. The mammary gland was dehydrated as described above, and mounted on a slide.

Example 6

Mammary Epithelial Cell Isolation and Culture

Mammary glands were removed from mice, washed in PBS, minced and incubated overnight at 37° C. in medium containing DMEM, 10% fetal bovine serum (FBS), 1.5% penicillin/streptomycin and 1 mg/ml of collagenase 1A (C9891, Sigma, St. Louis, Mo.). After dissociation and centrifugation, cells were grown on fetuin-coated plates in DMEM/F12 medium containing 15% FBS, 10 ng/ml epidermal growth factor, and 1 µg/ml insulin.

Example 7

Tissue Culture, Transfection and Adenoviral Infection

T47D cells were grown in DMEM/F12 medium (Invitrogen) containing 10% FBS and antibiotics at 37° C. in 5% CO2 incubator. MCF10A cells were cultured as described in Furuta et al., 2005, Proc. Natl. Acad. Sci. 102:9176. Transfection of cells was performed using Fugene 6 (Roche) or Lipofectamine Plus (Invitrogen). Cells were infected with adenovirus at a titer of $10^8$-$10^{10}$/ml by directly applying viruses into the growth medium at 5 multiplicities of infections (MOI). The infection efficiency was determined by direct visualization using fluorescent microscope of GFP-expressing cells after infection.

Example 8

Plasmid Constructs

Human plasmid constructs pCR3.1-PRA (for expression of PR-A protein) and pCR3.1-PRB (for expression of PR-B protein) were kindly provided by Dr. BW O'Malley at Baylor College of Medicine. pCMV-3xFlag-Bard1 was prepared by cloning a Bard1 PCR product into pCMV-3xFlag at sites of XbaI and NotI. pCHPLNIH-BRCA1 (wt, C61G and Q356R mutants) plasmids, and the adenovirus-based siRNA vectors against BRCA1 and luciferase were as described in Furuta 2005.

Example 9

Protein Lysate Preparation, SDS-PAGE and Immunoblotting

Cell and tissue lysates were prepared using EBC buffer (50 mM Tris-HCl, 120 mM NaCl, 1 mM EDTA, pH 8.0, 50 mM NaF, 0.5% NP-40). In general 50-100 µg of total protein lysates were separated on 8 or 10% SDS-polyacrylamide gels and transferred to polyvinylidene difluoride membranes (Millipore, Bedford, Mass.). Typically, membranes were stained with Ponceau S to confirm equal loading and transfer of protein. Immunoblotting was performed with following antibody: PR (rabbit polyclonal, C-19, sc-538, Santa Cruz Biotechnology, Santa Cruz, Calif.; dilution 1:2000), ERα (rabbit polyclonal, MC-20, and sc-542, Santa Cruz Biotechnology, Santa Cruz, Calif.; dilution 1:1000), HA (mouse ascitis, H9658, Sigma, 1:1000), BRCA1 antibody 6B4 was used as described (Furuta 2005).

Example 10

Inhibition of Proteasome Degradation and Determination of PR Half-Life

One day after plating, proliferating sub-confluent MECs or T47D cells were treated with 10 µM MG132 (BioMol Research Laboratories, Plymouth Meeting, Pa.) for 4 hr. Vehicle DMSO was added to the medium of untreated control cells. For the half-life study, 100 µg/ml of cyclohexamide (Sigma) was used and cells were harvested 0-6 hours after the addition of cyclohexamide. Cells were washed in PBS and protein lysates were prepared as described above.

Example 11

Ovariectomy and Hormone Treatments

Two weeks before steroid hormone treatment animals were bilaterally ovariectomized Mammary glands were stimulated to proliferate with daily subcutaneous injections of either 1 µg of estradiol (E2758, Sigma, St. Louis, Mo.) or 1 mg of progesterone (P8783, Sigma, St. Louis, Mo.) for 3 days. Untreated mice were used as controls.

Example 12

Anti-Progesterone Treatment Using Mifepristone Pellets

Nulliparous mature BRCA1$^{\Delta 11}$/p53$^{\Delta 5\&6}$ female mice, age 14-20 weeks, were anesthetized and pellets containing either 35 mg/60-day constant release of mifepristone (M8046, Sigma, St. Louis, Mo.) or placebo pellets (Innovative Research of America, Sarasota, Fla.) were implanted in the lateral side of the neck. Mice were monitored weekly for mammary tumors.

Example 13

Quantitative Real-Time PCR

Total RNA from MECs and mammary gland was extracted using TRIzol reagent (Invitrogen) and cDNA was synthesized using 2 µg of total RNA with the SuperScript preamplification system (Invitrogen). Primers used for Quantitative PCR are as follows:

```
PR total forward
                                  (SEQ ID NO: 1)
5'-CTGGGGTGGAGGTCGTACAAG-3', PR total reverse
                                  (SEQ ID NO: 2)
5'-ACCAATTGCCTTGATCAATTCG-3', PR-B forward
                                  (SEQ ID NO: 3)
5'-TCGTCTGTAGTCTCGCCTATACCG-3', PR-B reverse
                                  (SEQ ID NO: 4)
5'-CGGAGGGAGTCAACAACGAGT-3', GAPDH forward
                                  (SEQ ID NO: 5)
5'-CATTGACCTTCACTACATGGT-3', GAPDH reverse
                                  (SEQ ID NO: 6)
5'-ACCCTTCAAGTGAGCCCCAG-3', Bcl-xl forward
                                  (SEQ ID NO: 7)
5'-ACCGTTTGACACCACCAACAACAG-3', Bcl-xl reverse
                                  (SEQ ID NO: 8)
5'-TGGGTCCTTCGCTGGATTAGGTTT-3', mouse PR total forward
                                  (SEQ ID NO: 9)
5'-GGTGGAGGTCGTACAAGCAT-3', mouse PR total reverse
                                  (SEQ ID NO: 10)
5'-GGATTTGCCACATGGTAAGG-3', mouse PR-B forward
                                  (SEQ ID NO: 11)
5'-CGGAGAAGGACAGCAGACTC-3', mouse PR-B reverse
                                  (SEQ ID NO: 12)
5'-CCCAAAGAGACACCAGGAAG-3'.
```

For the detection of human PR, Bcl-Xl and GAPDH, primers were used as described in Ma et al., 2006, Mol. Endocrinol. 20:14. Quantitative real-time PCR was performed using the ABI PRISM 7700 (Applied Biosystems, Foster City, Calif.) and SYBR Green technology. 96-well optical plates with reaction mixes were heated for 2 min at 50° C. and 4 min at 95° C., followed by 40 cycles of PCR consisting of 15 sec at 95° C. and 20 sec at 63° C. At the end of the run, samples were heated to 95° C. with a ramp time of 10 sec to construct dissociation curves to check that single PCR product was obtained. PCR reactions were also analyzed by gel electrophoresis to confirm that a single product of the expected size was amplified. Validation experiments were performed to demonstrate that efficiencies of target and reference amplifications were approximately equal. The comparative CT method for relative quantification of gene expression described by Applied Biosystems was used to determine PR-A and PR-B expression levels. Experiments were carried out in triplicate for each data point. Sequence Detection Systems 1.7 software (Applied Biosystems, Foster City, Calif.) was used for data analysis.

Example 14

In Vivo Ubiquitination Assay

MCF10A cells were grown to 50% confluence and co-transfected with plasmids for the expression of HA-tagged ubiquitin, PR-A, and BRCA1 (wt or mutant). Forty-eight hr after transfection, cells were infected by adenoviruses that express siRNA targeting BRCA1 or luciferase for 24 hr. Before harvest, cells were treated with 10 μM MG132 for 2 hr, followed by incubation with 10 nM R5020 for 2 hr. Cells were harvested in a boiling solution of SDS (2% in Tris-buffered saline) and further disrupted by sonication. Lysates were diluted 10-fold with Triton X-100 solution (1% in Tris-buffered saline), incubated with protein A beads for 1 hr, and centrifuged. Supernatants were analyzed by immunoprecipitation and immunoblotting with the indicated antibodies.

Example 15

In Vitro Ubiquitination Assay 293T cells were co-transfected with plasmids expressing full length BRCA1 (wt or C61G mutant) and Flag-BARD1, or with pCMV-3xFlag vector alone as control. 20 mg of protein extract was immunoprecipitated with anti-Flag antibody and protein A Sepharose beads (150 μl) for overnight at 4° C. The beads were washed four times with washing buffer (300 mM NaCl, 0.5% Nonidet P-40, and phosphatase inhibitors), and then aliquoted (15 μl in dried volume) for the following binding assay.

PR-A protein was purified from extracts prepared from Sf9 cells infected with PR-baculovirus using Ni-NTA-based affinity purification (Qiagen), and pre-incubated (1 μg) with 20 μg extracts from Hela cells treated with EGF (50 ng/ml for 5 min) in a kinase buffer containing 50 mM Tris HCl (pH 7.4), 5 mM $MgCl_2$, 0.5 mM dithiothreitol, 5 mM NaF, 10 nM okadaic acid, 100 μM ATP at 30° C. for 30 min. The reaction products were added to BRCA1/BARD1 complex that was immobilized to protein A beads with anti-Flag antibody (15 μl in dried volume). The mixture was incubated at 4° C. for 60 min. The beads were then washed with buffer containing 150 mM NaCl, 0.5% NP-40, and phosphatase inhibitors and used for ubiquitination reaction. Ubiquitination reactions were carried out with a total volume of 30 μl containing 1 μg of ubiquitin, 20 ng of E1, and 250 ng of E2 as well as 2 mM Mg-ATP in the ubiquitination buffer (50 mM Tris-HCl, pH 7.4, 2 mM NaF, 10 nM okadaic acid, 0.6 mM DTT) at 37° C. for 60 min. Reaction was terminated by boiling the samples in SDS-sample buffer. The products were separated by SDS-PAGE, and analyzed by western blotting using anti-PR and anti-HA antibodies. Aliquots (10 μl) of the reactions were analyzed by immunoblotting using anti-Flag antibody.

Example 16

Combination Treatment of Mouse Tumors with Mifepristone, Tamoxifen and Fulvestrant Three to four month old $BRCA1^{\Delta 11}/p53^{\Delta 5\&6}$, $p53^{\Delta 5\&6}/p53^{\Delta 5\&6}$ and wt mice were injected with the following compounds; 50 μg/gram body weight of mifepristone (subcutaneous) alone or in combination with 20 mg/gram body weight of tamoxifen (intraperitoneal) or 50 μg/gram body weight of fulvestrant (intraperitoneal), tamoxifen alone (20 mg/gram body weight intraperitoneal), or fulvestrant alone (50 μg/gram body weight intraperitoneal). All mice were injected with the respective compounds for seven consecutive days, except for one of the $BRCA1^{\Delta 11}/p53^{\Delta 5\&6}$ mice that was injected with tamoxifen for fourteen instead of seven days, and all mice were sacrificed the day following the final injection. Mice were additionally injected with BrdU two hours prior to sacrifice. Control mice were injected with 70% ethanol. The number of mice used for each treatment group consisted of; 1) mifepristone alone-two wt, three $BRCA1^{\Delta 11}/p53^{\Delta 5\&6}$ and two $p53^{\Delta 5\&6}/p53^{\Delta 5\&6}$, 2) tamoxifen alone-two wt and two $BRCA1^{\Delta 11}/p53^{\Delta 5\&6}$, 3) fulvestrant alone-two $BRCA1^{\Delta 11}/p53^{\Delta 5\&6}$, 4) mifepristone and tamoxifen-two wt and four $BRCA1^{\Delta 11}/p53^{\Delta 5\&6}$, 5) mifepristone and fulvestrant-two $BRCA1^{\Delta 11}/p53^{\Delta 5\&6}$, 6) ethanol control-one each of wt and $BRCA1^{\Delta 11}/p53^{\Delta 5\&6}$.

Example 17

Early Preventive Treatment of Cancer in Subjects with BRCA1 Mutations

This Example describes the early administration of Progesterone Receptor antagonists to mice with a BRCA1 mutation to prevent or delay the development of tumors. Data from this Example is shown in FIG. 12.

The data developed during this example indicates a pellet containing 35 mg/60 day constant release mifepristone (RU-486) (n=14) for two months, exhibited effective prevention of tumor formation. Also tested was a pellet containing 5 mg or 35 mg/60 day constant releases of progesterone receptor modifier with a greater selectivity, CDB-2914 which showed that 35 mg/60 day has a preventative effect (n=4), similar to RU-486. However, 5 mg/60 days failed to show any efficacy (FIG. 12).

Figure 12:
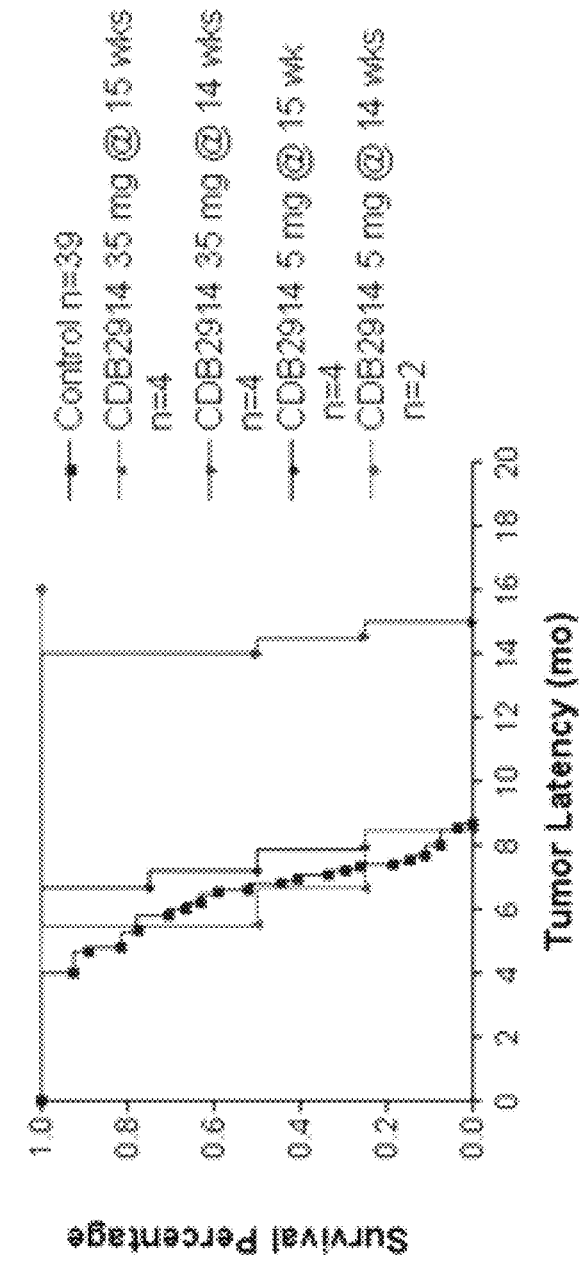
FIGS. 12A-C (A) Nulliparous $Brca1^{f/f}p53^{f/f}Crec$ mice, age 14-wk or 15-wk old, were implanted with a pellet containing 5 mg or 35 mg/60 day constant release CDB-2914. Mice were monitored weekly for palpable tumor. (B) Whole mount of mammary glands from a 6.5 month-old $Brca1^{f/f}p53^{f/f}Crec$ mouse without CDB-2914 treatment. Arrow indicates tumor foci in the gland. (C) CDB-2914 inhibits ductal branching of the mammary gland of $Brca1^{f/f}p53^{f/f}Crec$. Whole mount of mammary glands from a 7.0-month-old $Brca1^{f/f}p53^{f/f}Crec$ mouse treated with 35 mg/60 day constant releases CDB-2914 at the age of 14-wk-old.
Figure 12:
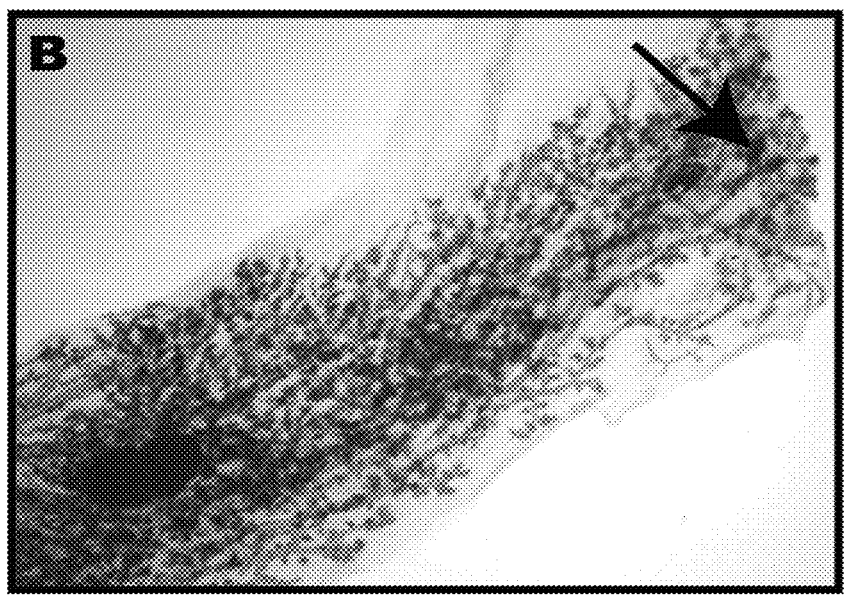
Figure 12:
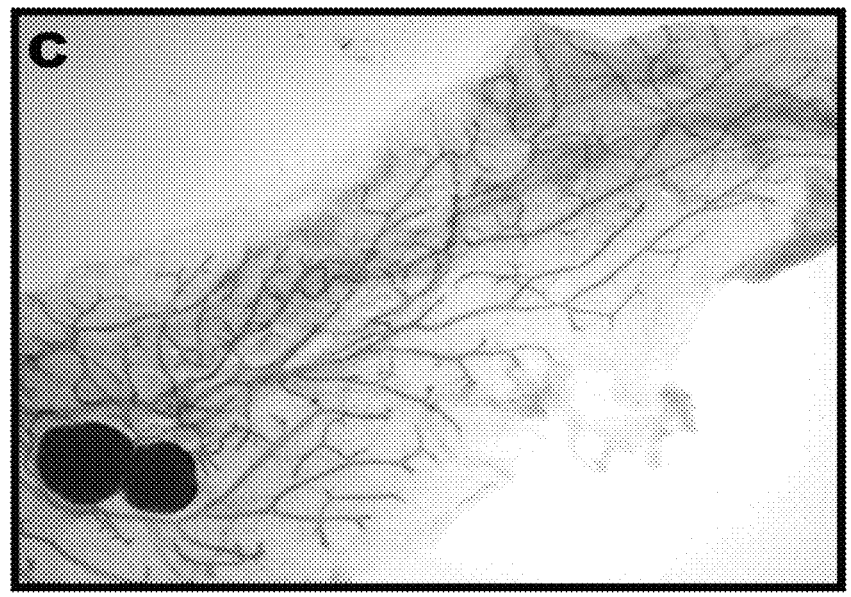

Two-month-release CDB-2914 pellet delayed development of palpable tumors if implanted before 14 weeks of age in a limited number of mice (n=4) but failed to do so if the pellet was placed after 15 wks (FIG. 12). An effective development window for prevention treatment has also been shown for RU-486 (data not shown). I would appear that the time window for treatment is important.

Three additional groups of mice could be treated with the protocol above, including 10-wk, 12-wk and 14-wk old mice. It is expected that the earlier treatment may further prevent tumor formation for a longer period of time.

In humans, the best timing for using progesterone receptor modulators in breast cancer prevention may be, for example, 5-10 years before prior to onset of malignant transformation in high-risk individuals. Based on studies of 1008 cases (King et al., New York Breast Cancer Study Group, Science. 302:643-6 (2003), very few BRCA1 carriers were diagnosed at age 30. Therefore, in some embodiments, age 20-25 is likely to be a good window for using progesterone receptor modulators in breast cancer prevention. Mifepristone and CDB-2914 have been approved for termination of pregnancy and emergency contraception, respectively, and several studies have tested their usage as long-term contraception (reviewed in Chabbert-Buffet, et al. Mol. Cell. Endocrino. 358: 232-243 (2012). Therefore, long-term usage in humans, of progesterone receptors at a young age (e.g., less than 35 or less than 30, or less than 25 years old) may be a suitable treatment for patients with BRCA1 mutations to delay or prevent the development of cancer (e.g., breast cancer). Such early, and long-term treatment, may be a suitable option for breast cancer patients that want to avoid, or cannot afford, a preventative double mastectomy.

All publications, Genbank sequences and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method for delaying the onset of progesterone receptor related cancers comprising:
   a) providing a human subject with a breast cancer gene 1 (BRCA1) mutation that is progesterone receptor related and a p53 mutation, wherein said subject has been diagnosed as possessing said BRCA1 mutation;
   b) providing a progesterone receptor antagonist, wherein said progesterone receptor antagonist comprises 17α-acetoxy-11β-(4-N,N-dimethylaminophenyl)-19-norpregna-4,9-diene-3,20-dione (CDB-2914), and
   c) treating said subject with said progesterone receptor antagonist thereby preventing or delaying the onset of said progesterone receptor related cancer.

2. The method of claim 1, wherein said progesterone receptor antagonist further comprises mifepristone (RU 486).

3. The method of claim 1, further comprising treating said subject with an additional chemopreventive agent.

4. The method of claim 3, wherein said chemopreventive agent is an anti-estrogen.

5. The method of claim 3, wherein said chemopreventive agent is an aromatase inhibitor.

6. The method of claim 4, wherein said anti-estrogen is tamoxifen.

7. The method of claim 4, wherein said anti-estrogen is fulvestrant.

8. A method for delaying the onset of progesterone receptor related cancers comprising:
   a) providing a human subject with a breast cancer gene 1 (BRCA1) mutation that is progesterone receptor related and a p53 mutation, wherein said subject has been diagnosed as possessing said BRCA1 mutation;
   b) providing a progesterone receptor antagonist, wherein said progesterone receptor antagonist comprises mifepristone (RU 486), and
   c) treating said subject with said progesterone receptor antagonist thereby preventing or delaying the onset of said progesterone receptor related cancer.

9. The method of claim 8, further comprising treating said subject with an additional chemopreventive agent.

10. The method of claim 9, wherein said chemopreventive agent is an anti-estrogen.

11. The method of claim 9, wherein said chemopreventive agent is an aromatase inhibitor.

12. The method of claim 11, wherein said anti-estrogen is tamoxifen.

13. The method of claim 11, wherein said anti-estrogen is fulvestrant.

* * * * *